United States Patent [19]
Bujard et al.

[11] Patent Number: 5,362,646
[45] Date of Patent: Nov. 8, 1994

[54] EXPRESSION CONTROL SEQUENCES

[75] Inventors: Hermann Bujard, Heidelberg; Michael Lanzer, Laudenbach, both of Germany

[73] Assignee: Hoffman-La Roche, Inc., Nutley, N.J.

[21] Appl. No.: 804,531

[22] Filed: Dec. 11, 1991

Related U.S. Application Data

[63] Continuation of Ser. No. 223,597, Jul. 25, 1988, abandoned.

[30] Foreign Application Priority Data

Aug. 17, 1987 [CH] Switzerland .................. 3152/87

[51] Int. Cl.$^5$ ............ C12N 15/00; C12N 15/72; C12N 15/11
[52] U.S. Cl. ............... 435/252.33; 435/69.1; 435/172.3; 435/320.1; 530/24.1; 935/29; 935/41; 935/43; 935/73
[58] Field of Search ........ 435/69.1, 172.3, 252.3, 435/252.31, 252.33, 320.1; 536/27, 24.1; 935/29, 41, 43, 72-74

[56] References Cited

FOREIGN PATENT DOCUMENTS

| | | | |
|---|---|---|---|
| 0041767 | 12/1981 | European Pat. Off. | 435/172.3 |
| 0067540 | 12/1982 | European Pat. Off. | 435/172.3 |
| 0130074 | 1/1985 | European Pat. Off. | 435/172.3 |
| 0138437 | 4/1985 | European Pat. Off. | 435/172.3 |
| 0186069 | 7/1986 | European Pat. Off. | 435/172.3 |
| 0207459 | 1/1987 | European Pat. Off. | 435/172.3 |
| 237675A | 7/1986 | Germany . | |

OTHER PUBLICATIONS

Itakura et al., Science 198:1056-1063 (1977).
Goeddel et al., Proc. Natl. Acad. Sci. USA 76:106-110 (1979).
Emtage et al., Nature 283:171-174 (1980).
Marital et al., Science 205:602-607 (1979).
Bernard et al., Gene 5:59-76 (1979).
Ammann et al., Gene 25:167-178 (1983).
de Boer et al., Proc. Natl. Acad. Sci. USA 80:21-25 (1983).
Hillen et al., J. Mol. Biol. 172:185-201 (1984).
Bujard et al., Methods in Enzymology 155:416-433 (1987).
Whitson and Matthews, Biochemistry 25:3845-3852 (1986).
Deuschle et al., EMBO J. 5:2987-2994 (1986).
Kammerer et al., EMBO J. 5:2995-3000 (1986).
*Genes IV*, Lewin, 1990, Oxford University Press, New York, N.Y., pp. 253-263.
Bujard et al; in Sequence Specificity in Transcription and Translation, 1985, Alan R. Liss, Inc., pp. 21-29.

*Primary Examiner*—James Martinell
*Attorney, Agent, or Firm*—George M. Gould; William H. Epstein; Bruce A. Pokras

[57] ABSTRACT

Expression control sequences are provided for the expression of pro- and eukaryotic proteins. These control sequences are produced by combining promoter sequences having a low signal strength and a high in vivo promoter strength and operator/repressor systems having a high association rate. Expression vectors containing such expression control sequences, microorganisms transformed with such expression vectors and methods for producing pro- and eukaryotic proteins using the expression control sequences, expression vectors and transformed microorganisms are also provided.

10 Claims, 37 Drawing Sheets

```
         10         20         30         40         50
         |          |          |          |          |
   1 GAATTCCTCG AGGAATTCCG GATCCGGCAT CATGGTTCGA CCATTGAACT
  51 GCATCGTCGC CGTGTCCCAA AATATGGGGA TTGGCAAGAA CGGAGACCTA
 101 CCCTGGCCTC CGCTCAGGAA CGAGTTCAAG TACTTCCAAA GAATGACCAC
 151 AACCTCTTCA GTGGAAGGTA ACAGAATCT GGTGATTATG GGTAGGAAAA
 201 CCTGGTTCTC CATTCCTGAG AAGAATCGAC CTTTAAAGGA CAGAATTAAT
 251 ATAGTTCTCA GTAGAGAACT CAAAGAACCA CCACGAGGAG CTCATTTTCT
 301 TGCCAAAAGT TTGGATGATG CCTTAAGACT TATTGAACAA CCGGAATTGG
 351 CAAGTAAAGT AGACATGGTT TGGATAGTCG GAGGCAGTTC TGTTTACCAG
 401 GAAGCCATGA ATCAACCAGG CCACCTTAGA CTCTTTGTGA CAAGGATCAT
 451 GCAGGAATTT GAAAGTGACA CGTTTTCCC AGAAATTGAT TTGGGGAAAT
 501 ATAAACTTCT CCCAGAATAC CCAGGCGTCC TCTCTGAGGT CCAGGAGGAA
 551 AAAGGCATCA AGTATAAGTT TGAAGTCTAC GAGAAGAAAG ACTAACAGGA
 601 AGATGCTTTC AAGTTCTCTG CTCCCCTCCT AAAGCTATGC ATTTTTATAA
 651 GACCATGGGA CTTTTGCTGG CTTTAGATCC GGCCAAGCTT GGACTCCTGT
 701 TGATAGATCC AGTAATGACC TCAGAACTCC ATCTGGATTT GTTCAGAACG
 751 CTCGGTTGCC GCCGGGCGTT TTTTATTGGT GAGAATCCAA GCTTGGCGAG
 801 ATTTTCAGGA GCTAAGGAAG CTAAAATGGA GAAAAAAATC ACTGGATATA
 851 CCACCGTTGA TATATCCCAA TGGCATCGTA AAGAACATTT TGAGGCATTT
 901 CAGTCAGTTG CTCAATGTAC CTATAACCAG ACCGTTCAGC TGGATATTAC
 951 GGCCTTTTTA AAGACCGTAA AGAAAAATAA GCACAAGTTT TATCCGGCCT
1001 TTATTCACAT TCTTGCCCGC CTGATGAATG CTCATCCGGA ATTCCGTATG
1051 GCAATGAAAG ACGGTGAGCT GGTGATATGG GATAGTGTTC ACCCTTGTTA
1101 CACCGTTTTC CATGAGCAAA CTGAAACGTT TTCATCGCTC TGGAGTGAAT
1151 ACCACGACGA TTTCCGGCAG TTTCTACACA TATATTCGCA AGATGTGGCG
```

FIG. 1b

1201 TGTTACGGTG AAAACCTGGC CTATTTCCCT AAAGGGTTTA TTGAGAATAT
1251 GTTTTTCGTC TCAGCCAATC CCTGGGTGAG TTTCACCAGT TTTGATTTAA
1301 ACGTGGCCAA TATGGACAAC TTCTTCGCCC CCGTTTTCAC CATGGGCAAA
1351 TATTATACGC AAGGCGACAA GGTGCTGATG CCGCTGGCGA TTCAGGTTCA
1401 TCATGCCGTC TGTGATGGCT TCCATGTCGG CAGAATGCTT AATGAATTAC
1451 AACAGTACTG CGATGAGTGG CAGGGCGGGG CGTAATTTTT TTAAGGCAGT
1501 TATTGGTGCC CTTAAACGCC TGGGGTAATG ACTCTCTAGA GCTGCCTCGC
1551 GCGTTTCGGT GATGACGGTG AAAACCTCTG ACACATGCAG CTCCCGGAGA
1601 CGGTCACAGC TTGTCTGTAA GCGGATGCCG GGAGCAGACA AGCCCGTCAG
1651 GGCGCGTCAG CGGGTGTTGG CGGGTGTCGG GCGCAGCCA TGACCCAGTC
1701 ACGTAGCGAT AGCGGAGTGT ATACTGGCTT AACTATGCGG CATCAGAGCA
1751 GATTGTACTG AGAGTGCACC ATATGCGGTG TGAAATACCG CACAGATGCG
1801 TAAGGAGAAA ATACCGCATC AGGCGCTCTT CCGCTTCCTC GCTCACTGAC
1851 TCGCTGCGCT CGGTCTGTCG GCTGCGGCGA GCGGTATCAG CTCACTCAAA
1901 GGCGGTAATA CGGTTATCCA CAGAATCAGG GGATAACGCA GGAAAGAACA
1951 TGTGAGCAAA AGGCCAGCAA AAGGCCAGGA ACCGTAAAAA GGCCGCGTTG
2001 CTGGCGTTTT TCCATAGGCT CCGCCCCCCT GACGAGCATC ACAAAAATCG
2051 ACGCTCAAGT CAGAGGTGGC GAAACCCGAC AGGACTATAA AGATACCAGG
2101 CGTTTCCCCC TGGAAGCTCC CTCGTGCGCT CTCCTGTTCC GACCCTGCCG
2151 CTTACCGGAT ACCTGTCCGC CTTTCTCCCT TCGGGAAGCG TGGCGCTTTC
2201 TCAATGCTCA CGCTGTAGGT ATCTCAGTTC GGTGTAGGTC GTTCGCTCCA
2251 AGCTGGGCTG TGTGCACGAA CCCCCCGTTC AGCCCGACCG CTGCGCCTTA
2301 TCCGGTAACT ATCGTCTTGA GTCCAACCCG GTAAGACACG ACTTATCGCC
2351 ACTGGCAGCA GCCACTGGTA ACAGGATTAG CAGAGCGAGG TATGTAGGCG
2401 GTGCTACAGA GTTCTTGAAG TGGTGGCCTA ACTACGGCTA CACTAGAAGG
2451 ACAGTATTTG GTATCTGCGC TCTGCTGAAG CCAGTTACCT TCGGAAAAAG
2501 AGTTGGTAGC TCTTGATCCG GCAAACAAAC CACCGCTGGT AGCGGTGGTT

FIG. 1c

```
2551 TTTTTGTTTG CAAGCAGCAG ATTACGCGCA GAAAAAAAGG ATCTCAAGAA
2601 GATCCTTTGA TCTTTTCTAC GGGGTCTGAC GCTCAGTGGA ACGAAAACTC
2651 ACGTTAAGGG ATTTTGGTCA TGAGATTATC AAAAAGGATC TTCACCTAGA
2701 TCCTTTTAAA TTAAAAATGA AGTTTTAAAT CAATCTAAAG TATATATGAG
2751 TAAACTTGGT CTGACAGTTA CCAATGCTTA ATCAGTGAGG CACCTATCTC
2801 AGCGATCTGT CTATTTCGTT CATCCATAGC TGCCTGACTC CCCGTCGTGT
2851 AGATAACTAC GATACGGGAG GGCTTACCAT CTGGCCCCAG TGCTGCAATG
2901 ATACCGCGAG ACCCACGCTC ACCGGCTCCA GATTTATCAG CAATAAACCA
2951 GCCAGCCGGA AGGGCCGAGC GCAGAAGTGG TCCTGCAACT TTATCCGCCT
3001 CCATCCAGTC TATTAATTGT TGCCGGGAAG CTAGAGTAAG TAGTTCGCCA
3051 GTTAATAGTT TGCGCAACGT TGTTGCCATT GCTGCAGGCA TCGTGGTGTC
3101 ACGCTCGTCG TTTGGTATGG CTTCATTCAG CTCCGGTTCC CAACGATCAA
3151 GGCGAGTTAC ATGATCCCCC ATGTTGTGCA AAAAAGCGGT TAGCTCCTTC
3201 GGTCCTCCGA TCGTTGTCAG AAGTAAGTTG GCCGCAGTGT TATCACTCAT
3251 GGTTATGGCA GCACTGCATA ATTCTCTTAC TGTCATGCCA TCCGTAAGAT
3301 GCTTTTCTGT GACTGGTGAG TACTCAACCA AGTCATTCTG AGAATAGTGT
3351 ATGCGGCGAC CGAGTTGCTC TTGCCCGGCG TCAACACGGG ATAATACCGC
3401 GCCACATAGC AGAACTTTAA AAGTGCTCAT CATTGGAAAA CGTTCTTCGG
3451 GGCGAAAACT CTCAAGGATC TTACCGCTGT TGAGATCCAG TTCGATGTAA
3501 CCCACTCGTG CACCCAACTG ATCTTCAGCA TCTTTTACTT TCACCAGCGT
3551 TTCTGGGTGA GCAAAAACAG GAAGGCAAAA TGCCGCAAAA AAGGGAATAA
3601 GGGCGACACG GAAATGTTGA ATACTCATAC TCTTCCTTTT TCAATATTAT
3651 TGAAGCATTT ATCAGGGTTA TTGTCTCATG AGCGGATACA TATTTGAATG
3701 TATTTAGAAA AATAAACAAA TAGGGGTTCC GCGCACATTT CCCCGAAAAG
3751 TGCCACCTGA CGTCTAAGAA ACCATTATTA TCATGACATT AACCTATAAA
3801 AATAGGCGTA TCACGAGGCC CTTTCGTCTT CAA
```

F I G. ld

```
              10         20         30         40         50
    1 CCTCGACGTC GACGTTAACG GTACCGAGCT TGTGGCAGTT TAAGGCGGGC
   51 GTCCTGCCCG CCACCCTCCG GGCCGTTGCT TCGCAACGTT CAAATCCGCT
  101 CCCGGCGGAT TTGTCCTACT CAGGAGAGCG TTCACCGACA AACAACAGAT
  151 AAAACGAAAG GCCCAGTCTT TCGACTGAGC CTTTCGTTTT ATTTGATGCC
  201 TCAAGCTCGG TACCTCGAGG GAATTCCGGA TCCGGCATCA TGGTTCGACC
  251 ATTGAACTGC ATCGTCGCCG TGTCCCAAAA TATGGGGATT GGCAAGAACG
  301 GAGACCTACC CTGGCCTCCG CTCAGGAACG AGTTCAAGTA CTTCCAAAGA
  351 ATGACCACAA CCTCTTCAGT GGAAGGTAAA CAGAATCTGG TGATTATGGG
  401 TAGGAAAACC TGGTTCTCCA TTCCTGAGAA GAATCGACCT TTAAAGGACA
  451 GAATTAATAT AGTTCTCAGT AGAGAACTCA AAGAACCACC ACGAGGAGCT
  501 CATTTTCTTG CCAAAAGTTT GGATGATGCC TTAAGACTTA TTGAACAACC
  551 GGAATTGGCA AGTAAAGTAG ACATGGTTTG GATAGTCGGA GGCAGTTCTG
  601 TTTACCAGGA AGCCATGAAT CAACCAGGCC ACCTTAGACT CTTTGTGACA
  651 AGGATCATGC AGGAATTTGA AAGTGACACG TTTTTCCCAG AAATTGATTT
  701 GGGGAAATAT AAACTTCTCC CAGAATACCC AGGCGTCCTC TCTGAGGTCC
  751 AGGAGGAAAA AGGCATCAAG TATAAGTTTG AAGTCTACGA GAAGAAAGAC
  801 TAACAGGAAG ATGCTTTCAA GTTCTCTGCT CCCCTCCTAA AGCTATGCAT
  851 TTTTATAAGA CCATGGGACT TTGCTGGCT  TTAGATCCGG CCAAGCTTGG
  901 ACTCCTGTTG ATAGATCCAG TAATGACCTC AGAACTCCAT CTGGATTTGT
  951 TCAGAACGCT CGGTTGCCGC CGGGCGTTTT TTATTGGTGA GAATCCAAAG
 1001 CTTGGCGAGA TTTTCAGGAG CTAAGGAAGC TAAAATGGAG AAAAAAATCA
 1051 CTGGATATAC CACCGTTGAT ATATCCCAAT GGCATCGTAA AGAACATTTT
 1101 GAGGCATTTC AGTCAGTTGC TCAATGTACC TATAACCAGA CCGTTCAGCT
 1151 GGATATTACG GCCTTTTTAA AGACCGTAAA GAAAAATAAG CACAAGTTTT
 1201 ATCCGGCCTT TATTCACATT CTTGCCCGCC TGATGAATGC TCATCCGGAA
 1251 TTCCGTATGG CAATGAAAGA CGGTGAGCTG GTGATATGGG ATAGTGTTCA
```

FIG. 2b

1301 CCCTTGTTAC ACCGTTTTCC ATGAGCAAAC TGAAACGTTT TCATCGCTCT

1351 GGAGTGAATA CCACGACGAT TTCCGGCAGT TTCTACACAT ATATTCGCAA

1401 GATGTGGCGT GTTACGGTGA AAACCTGGCC TATTTCCCTA AGGGTTTAT

1451 TGAGAATATG TTTTTCGTCT CAGCCAATCC CTGGGTGAGT TTCACCAGTT

1501 TTGATTTAAA CGTGGCCAAT ATGGACAACT TCTTCGCCCC CGTTTTCACC

1551 ATGGGCAAAT ATTATACGCA AGGCGACAAG GTGCTGATGC CGCTGGCGAT

1601 TCAGGTTCAT CATGCCGTCT GTGATGGCTT CCATGTCGGC AGAATGCTTA

1651 ATGAATTACA ACAGTACTGC GATGAGTGGC AGGGCGGGGC GTAATTTTT

1701 TAAGGCAGTT ATTGGTGCCC TTAAACGCCT GGGGTAATGA CTCTCTAGAG

1751 CTGCCTCGCG CGTTTCGGTG ATGACGGTGA AAACCTCTGA CACATGCAGC

1801 TCCCGGAGAC GGTCACAGCT TGTCTGTAAG CGGATGCCGG GAGCAGACAA

1851 GCCCGTCAGG GCGCGTCAGC GGGTGTTGGC GGGTGTCGGG GCGCAGCCAT

1901 GACCCAGTCA CGTAGCGATA GCGGAGTGTA TACTGGCTTA ACTATGCGGC

1951 ATCAGAGCAG ATTGTACTGA GAGTGCACCA TATGCGGTGT GAAATACCGC

2001 ACAGATGCGT AAGGAGAAAA TACCGCATCA GGCGCTCTTC CGCTTCCTCG

2051 CTCACTGACT CGCTGCGCTC GGTCGTTCGG CTGCGGCGAG CGGTATCAGC

2101 TCACTCAAAG GCGGTAATAC GGTTATCCAC AGAATCAGGG GATAACGCAG

2151 GAAAGAACAT GTGAGCAAAA GGCCAGCAAA AGGCCAGGAA CCGTAAAAAG

2201 GCCGCGTTGC TGGCGTTTTT CCATAGGCTC CGCCCCCCTG ACGAGCATCA

2251 CAAAAATCGA CGCTCAAGTC AGAGGTGGCG AAACCCGACA GGACTATAAA

2301 GATACCAGGC GTTTCCCCCT GGAAGCTCCC TCGTGCGCTC TCCTGTTCCG

2351 ACCCTGCCGC TTACCGGATA CCTGTCCGCC TTTCTCCCTT CGGGAAGCGT

2401 GGCGCTTTCT CAATGCTCAC GCTGTAGGTA TCTCAGTTCG GTGTAGGTCG

2451 TTCGCTCCAA GCTGGGCTGT GTGCACGAAC CCCCGTTCA GCCCGACCGC

2501 TGCGCCTTAT CCGGTAACTA TCGTCTTGAG TCCAACCCGG TAAGACACGA

2551 CTTATCGCCA CTGGCAGCAG CCACTGGTAA CAGGATTAGC AGAGCGAGGT

2601 ATGTAGGCGG TGCTACAGAG TTCTTGAAGT GGTGGCCTAA CTACGGCTAC

FIG. 2c

2651 ACTAGAAGGA CAGTATTTGG TATCTGCGCT CTGCTGAAGC CAGTTACCTT
2701 CGGAAAAAGA GTTGGTAGCT CTTGATCCGG CAAACAAACC ACCGCTGGTA
2751 GCGGTGGTTT TTTTGTTTGC AAGCAGCAGA TTACGCGCAG AAAAAAAGGA
2801 TCTCAAGAAG ATCCTTTGAT CTTTTCTACG GGTCTGACG CTCAGTGGAA
2851 CGAAAACTCA CGTTAAGGGA TTTTGGTCAT GAGATTATCA AAAGGATCT
2901 TCACCTAGAT CCTTTTAAAT TAAAAATGAA GTTTTAAATC AATCTAAAGT
2951 ATATATGAGT AAACTTGGTC TGACAGTTAC CAATGCTTAA TCAGTGAGGC
3001 ACCTATCTCA GCGATCTGTC TATTTCGTTC ATCCATAGTT GCCTGACTCC
3051 CCGTCGTGTA GATAACTACG ATACGGGAGG GCTTACCATC TGGCCCCAGT
3101 GCTGCAATGA TACCGCGAGA CCCACGCTCA CCGGCTCCAG ATTTATCAGC
3151 AATAAACCAG CCAGCCGGAA GGGCCGAGCG CAGAAGTGGT CCTGCAACTT
3201 TATCCGCCTC CATCCAGTCT ATTAATTGTT GCCGGGAAGC TAGAGTAAGT
3251 AGTTCGCCAG TTAATAGTTT GCGCAACGTT GTTGCCATTG CTGCAGGCAT
3301 CGTGGTGTCA CGCTCGTCGT TTGGTATGGC TTCATTCAGC TCCGGTTCCC
3351 AACGATCAAG GCGAGTTACA TGATCCCCCA TGTTGTGCAA AAAAGCGGTT
3401 AGCTCCTTCG GTCCTCCGAT CGTTGTCAGA AGTAAGTTGG CCGCAGTGTT
3451 ATCACTCATG GTTATGGCAG CACTGCATAA TTCTCTTACT GTCATGCCAT
3501 CCGTAAGATG CTTTTCTGTG ACTGGTGAGT ACTCAACCAA GTCATTCTGA
3551 GAATAGTGTA TGCGGCGACC GAGTTGCTCT TGCCCGGCGT CAACACGGGA
3601 TAATACCGCG CCACATAGCA GAACTTTAAA AGTGCTCATC ATTGGAAAAC
3651 GTTCTTCGGG GCGAAAACTC TCAAGGATCT TACCGCTGTT GAGATCCAGT
3701 TCGATGTAAC CCACTCGTGC ACCCAACTGA TCTTCAGCAT CTTTTACTTT
3751 CACCAGCGTT TCTGGGTGAG CAAAAACAGG AAGGCAAAAT GCCGCAAAAA
3801 AGGGAATAAG GGCGACACGG AAATGTTGAA TACTCATACT CTTCCTTTTT
3851 CAATATTATT GAAGCATTTA TCAGGGTTAT TGTCTCATGA GCGGATACAT
3901 ATTTGAATGT ATTTAGAAAA ATAAACAAAT AGGGGTTCCG CGCACATTTC
3951 CCCGAAAAGT GCCACCTGAC GTCTAAGAAA CCATTATTAT CATGACATTA
4001 ACCTATAAAA ATAGGCGTAT CACGAGGCCC TTTCGTCTTC A

FIG. 2d

```
                  10         20         30         40         50
    1 GAATTC.... .......... .......... .......... ..........
   51 .......... .......... .......... .......... ..........
  101 .......... .......... .......... .......... ..........
  151 GAATTC.... .......... .......... ........AAA TAGTACATAA
  201 TGGATTTCCT TACGCGAAAT ACGGGCAGAC ATGGCCTGCC CGGTTATTAT
  251 TATTTTTGAC ACCAGACCAA CTGGTAATGG TAGCGACCGG CGCTCAGCTG
  301 GAATTCCGCC GATACTGACG GGCTCCAGGA GTCGTCGCCA CCAATCCCCA
  351 TATGGAAACC GTCGATATTC AGCCATGTGC CTTCTTCCGC GTGCAGCAGA
  401 TGGCGATGGC TGGTTTCCAT CAGTTGCTGT TGACTGTAGC GGCTGATGTT
  451 GAACTGGAAG TCGCCGCGCC ACTGGTGTGG GCCATAATTC AATTCGCGCG
  501 TCCCGCAGCG CAGACCGTTT TCGCTCGGGA AGACGTACGG GGTATACATG
  551 TCTGACAATG GCAGATCCCA GCGGTCAAAA CAGGCGGCAG TAAGGCGGTC
  601 GGGATAGTTT TCTTGCGGCC CTAATCGAG CCAGTTTACC CGCTCTGCTA
  651 CCTGCGCCAG CTGGCAGTTC AGGCCAATCC GCGCCGGATG CGGTGTATCG
  701 CTCGCCACTT CAACATCAAC GGTAATCGCC ATTTGACCAC TACCATCAAT
  751 CCGGTAGGTT TTCCGGCTGA TAAATAAGGT TTTCCCCTGA TGCTGCCACG
  801 CGTGAGCGGT CGTAATCAGC ACCGCATCAG CAAGTGTATC TGCCGTGCAC
  851 TGCAACAACG CTGCTTCGGC CTGGTAATGG CCCGCCGCCT TCCAGCGTTC
  901 GACCCAGGCG TTAGGGTCAA TGCGGGTCGC TTCACTTACG CCAATGTCGT
  951 TATCCAGCGG TGCACGGGTG AACTGATCGC GCAGCGGCGT CAGCAGTTGT
 1001 TTTTTATCGC CAATCCACAT CTGTGAAAGA AAGCCTGACT GGCGGTTAAA
 1051 TTGCCAACGC TTATTACCCA GCTCGATGCA AAAATCCATT TCGCTGGTGG
 1101 TCAGATGCGG GATGGCGTGG GACGCGGCGG GGAGCGTCAC ACTGAGGTTT
 1151 TCCGCCAGAC GCCACTGCTG CCAGGCGCTG ATGTGCCCGG CTTCTGACCA
 1201 TGCGGTCGCG TTCGGTTGCA CTACGCGTAC TGTGAGCCAG AGTTGCCCGG
 1251 CGCTCTCCGG CTGCGGTAGT TCAGGCAGTT CAATCAACTG TTTACCTTGT
```

FIG. 3b

```
1301 GGAGCGACAT CCAGAGGCAC TTCACCGCTT GCCAGCGGCT TACCATCCAG
1351 CGCCACCATC CAGTGCAGGA GCTCGTTATC GCTATGACGG AACAGGTATT
1401 CGCTGGTCAC TTCGATGGTT TGCCCGGATA ACGGAACTG GAAAAACTGC
1451 TGCTGGTGTT TTGCTTCCGT CAGCGCTGGA TGCGGCGTGC GGTCGGCAAA
1501 GACCAGACCG TTCATACAGA ACTGGCGATC GTTCGGCGTA TCGCCAAAAT
1551 CACCGCCGTA AGCCGACCAC GGGTTGCCGT TTTCATCATA TTTAATCAGC
1601 GACTGATCCA CCCAGTCCCA GACGAAGCCG CCCTGTAAAC GGGGATACTG
1651 ACGAAACGCC TGCCAGTATT TAGCGAAACC GCCAAGACTG TTACCCATCG
1701 CGTGGGCGTA TTCGCAAAGG ATCAGCGGGC GCGTCTCTCC AGGTAGCGAA
1751 AGCCATTTTT TGATGGACCA TTTCGGCACA GCCGGGAAGG CTGGTCTTC
1801 ATCCACGCGC GCGTACATCG GCAAATAAT ATCGGTGGCC GTGGTGTCGG
1851 CTCCGCCGCC TTCATACTGC ACCGGGCGGG AAGGATCGAC AGATTTGATC
1901 CAGCGATACA GCGCGTCGTG ATTAGCGCCG TGGCCTGATT CATTCCCCAG
1951 CGACCAGATG ATCACACTCG GGTGATTACG ATCGCGCTGC ACCATTCGCG
2001 TTACGCGTTC GCTCATCGCC GGTAGCCAGC GCGGATCATC GGTCAGACGA
2051 TTCATTGGCA CCATGCCGTG GGTTTCAATA TTGGCTTCAT CCACCACATA
2101 CAGGCCGTAG CGGTCGCACA GCGTGTACCA CAGCGGATGG TTCGGATAAT
2151 GCGAACAGCG CACGGCGTTA AGTTGTTCT GCTTCATCAG CAGGATATCC
2201 TGCACCATCG TCTGCTCATC CATGACCTGA CCATGCAGAG GATGATGCTC
2251 GTGACGGTTA ACGCCTCGAA TCAGCAACGG CTTGCCGTTC AGCAGCAGCA
2301 GACCATTTTC AATCCGCACC TCGCGGAAAC CGACATCGCA GGCTTCTGCT
2351 TCAATCAGCG TGCCGTCGGC GGTGTGCAGT TCAACCACCG CACGATAGAG
2401 ATTCGGGATT TCGGCGCTCC ACAGTTTCGG GTTTTCGACG TTCAGACGTA
2451 GTGTGACGCG ATCGGCATAA CCACCACGCT CATCGATAAT TTCACCGCCG
2501 AAAGGCGCGG TGCCGCTGGC GACCTGCGTT TCACCCTGCC ATAAAGAAAC
2551 TGTTACCCGT AGGTAGTCAC GCAACTCGCC GCACATCTGA ACTTCAGCCT
2601 CCAGTACAGC GCGGCTGAAA TCATCATTAA AGCGAGTGGC AACATGGAAA
```

FIG. 3c

2651 TCGCTGATTT GTGTAGTCGG TTTATGCAGC AACGAGACGT CACGGAAAAT

2701 GCCGCTCATC CGCCACATAT CCTGATCTTC CAGATAACTG CCGTCACTCC

2751 AACGCAGCAC CATCACCGCG AGGCGGTTTT CTCCGGCGCG TAAAAATGCG

2801 CTCAGGTCAA ATTCAGACGG CAAACGACTG TCCTGGCCGT AACCGACCCA

2851 GCGCCCGTTG CACCACAGAT GAAACGCCGA GTTAACGCCA TCAAAAATAA

2901 TTCGCGTCTG GCCTTCCTGT AGCCAGCTTT CATCAACATT AAATGTGAGC

2951 GAGTAACAAC CCGTCGGATT CTCCGTGGGA ACAAACGGCG GATTGACCGT

3001 AATGGGATAG GTTACGTTGG TGTAGATGGG CGCATCGTAA CCGTGCATCT

3051 GCCAGTTTGA GGGGACGACG ACAGTATCGG CCTCAGGAAG ATCGCACTCC

3101 AGCCAGCTTT CCGGCACCGC TTCTGGTGCC GGAAACCAGG CAAAGCGCCA

3151 TTCGCCATTC AGGCTGCGCA ACTGTTGGGA AGGGCGATCG GTGCGGGCCT

3201 CTTCGCTATT ACGCCAGCTG GCGAAAGGGG GATGTGCTGC AAGGCGATTA

3251 AGTTGGGTAA CGCCAGGGTT TTCCCAGTCA CGACGTTGTA AAACGACGGC

3301 CAGTGAATCC GTAATCATGG TCATAGCTGT TTCCTGTGTG AATTCTGTGT

3351 GAAATTGTTA TCCGCTCACA ATTCCACACA ACATACGAGC CGGAAGCATA

3401 AAGTGTAAAG CCTGGGGTGC CTAATGAGTG AGCTAACTCA CATTAATTGC

3451 GTTGCCTCGA GGTACCTTAT AAACGCAGAA AGGCCCACCC GAAGGTGAGC

3501 CAGTTAACGT CGACAATTCG CGCTAACTTA CATTAATTGC GTTGCGCTCA

3551 CTGCCCGCTT TCCAGTCGGG AAACCTGTCG TGCCAGCTGC ATTAATGAAT

3601 CGGCCAACGC GCGGGGAGAG GCGGTTTGCG TATTGGGCGC CAGGGTGGTT

3651 TTTCTTTTCA CCAGTGAGAC GGGCAACAGC TGATTGCCCT TCACCGCCTG

3701 GCCCTGAGAG AGTTGCAGCA AGCGGTCCAC GCTGGTTTGC CCCAGCAGGC

3751 GAAAATCCTG TTTGATGGTG GTTAACGGCG GATATAACA TGAGCTGTCT

3801 TCGGTATCGT CGTATCCCAC TACCGAGATA TCCGCACCAA CGCGCAGCCC

3851 GGACTCGGTA ATGGCGCGCA TTGCGCCCAG CGCCATCTGA TCGTTGGCAA

3901 CCAGCATCGC AGTGGGAACG ATGCCCTCAT TCAGCATTTG CATGGTTTGT

3951 TGAAAACCGG ACATGGCACT CCAGTCGCCT TCCCGTTCCG CTATCGGCTG

FIG. 3d

```
4001 AATTTGATTG CGAGTGAGAT ATTTATGCCA GCCAGCCAGA CGCAGACGCG
4051 CCGAGACAGA ACTTAATGGG CCCGCTAACA GCGCGATTTG CTGGTGACCC
4101 AATGCGACCA GATGCTCCAC GCCCAGTCGC GTACCGTCTT CATGGGAGAA
4151 AATAATACTG TTGATGGGTG TCTGGTCAGA GACATCAAGA AATAACGCCG
4201 GAACATTAGT GCAGGCAGCT TCCACAGCAA TGGCATCCTG GTCATCCAGC
4251 GGATAGTTAA TGATCAGCCC ACTGACGCGT TGCGCGAGAA GATTGTGCAC
4301 CGCCGCTTTA CAGGCTTCGA CGCCGCTTCG TTCTACCATC GACACCACCA
4351 CGCTGGCACC CAGTTGATCG GCGCGAGATT TAATCGCCGC GACAATTTGC
4401 GACGGCGCGT GCAGGGCCAG ACTGGAGGTG GCAACGCCAA TCAGCAACGA
4451 CTGTTTGCCC GCCAGTTGTT GTGCCACGCG GTTGGGAATG TAATTCAGCT
4501 CCGCCATCGC CGCTTCCACT TTTTCCCGCG TTTTCGCAGA AACGTGGCTG
4551 GCCTGGTTCA CCACGCGGGA AACGGTCTGA TAAGAGACAC CGGCATACTC
4601 TGCGACATCG TATAACGTTA CTGGTTTCAC ATTCACCACC CTGAATTGAC
4651 TCTCTTCCGG GCGCTATCAT GCCATACCGC GAAAGGTTTT GCACCATTCG
4701 ATGGTGTCAA CGTAAATGCA TGCCGCTTCG CCTTCGCGCG CGAATTGTCG
4751 ACTAGAGCTG CCTCGCGCGT TTCGGTGATG ACGGTGAAAA CCTCTGACAC
4801 ATGCAGCTCC CGGAGACGGT CACAGCTTGT CTGTAAGCGG ATGCCGGGAG
4851 CAGACAAGCC CGTCAGGGCG CGTCAGCGGG TGTTGGCGGG TGTCGGGGCG
4901 CAGCCATGAC CCAGTCACGT AGCGATAGCG GAGTGTATAC TGGCTTAACT
4951 ATGCGGCATC AGAGCAGATT GTACTGAGAG TGCACCATAT GCGGTGTGAA
5001 ATACCGCACA GATGCGTAAG GAGAAAATAC CGCATCAGGC GCTCTTCCGC
5051 TTCCTCGCTC ACTGACTCGC TGCGCTCGGT CGTTCGGCTG CGGCGAGCGG
5101 TATCAGCTCA CTCAAAGGCG GTAATACGGT TATCCACAGA ATCAGGGGAT
5151 AACGCAGGAA AGAACATGTG AGCAAAAGGC CAGCAAAAGG CCAGGAACCG
5201 TAAAAAGGCC GCGTTGCTGG CGTTTTTCCA TAGGCTCCGC CCCCCTGACG
5251 AGCATCACAA AAATCGACGC TCAAGTCAGA GGTGGCGAAA CCCGACAGGA
5301 CTATAAAGAT ACCAGGCGTT TCCCCCTGGA AGCTCCCTCG TGCGCTCTCC
```

FIG. 3e

```
5351 TGTTCCGACC CTGCCGCTTA CCGGATACCT GTCCGCCTTT CTCCCTTCGG
5401 GAAGCGTGGC GCTTTCTCAA TGCTCACGCT GTAGGTATCT CAGTTCGGTG
5451 TAGGTCGTTC GCTCCAAGCT GGGCTGTGTG CACGAACCCC CCGTTCAGCC
5501 CGACCGCTGC GCCTTATCCG GTAACTATCG TCTTGAGTCC AACCCGGTAA
5551 GACACGACTT ATCGCCACTG GCAGCAGCCA CTGGTAACAG GATTAGCAGA
5601 GCGAGGTATG TAGGCGGTGC TACAGAGTTC TTGAAGTGGT GGCCTAACTA
5651 CGGCTACACT AGAAGGACAG TATTTGGTAT CTGCGCTCTG CTGAAGCCAG
5701 TTACCTTCGG AAAAAGAGTT GGTAGCTCTT GATCCGGCAA ACAAACCACC
5751 GCTGGTAGCG GTGGTTTTTT TGTTTGCAAG CAGCAGATTA CGCGCAGAAA
5801 AAAAGGATCT CAAGAAGATC CTTTGATCTT TTCTACGGGG TCTGACGCTC
5851 AGTGGAACGA AAACTCACGT TAAGGGATTT TGGTCATGAG ATTATCAAAA
5901 AGGATCTTCA CCTAGATCCT TTTAAATTAA AAATGAAGTT TTAAATCAAT
5951 CTAAAGTATA TATGAGTAAA CTTGGTCTGA CAGTTACCAA TGCTTAATCA
6001 GTGAGGCACC TATCTCAGCG ATCTGTCTAT TTCGTTCATC CATAGTTGCC
6051 TGACTCCCCG TCGTGTAGAT AACTACGATA CGGGAGGGCT TACCATCTGG
6101 CCCCAGTGCT GCAATGATAC CGCGAGACCC ACGCTCACCG GCTCCAGATT
6151 TATCAGCAAT AAACCAGCCA GCCGGAAGGG CCGAGCGCAG AAGTGGTCCT
6201 GCAACTTTAT CCGCCTCCAT CCAGTCTATT AATTGTTGCC GGGAAGCTAG
6251 AGTAAGTAGT TCGCCAGTTA ATAGTTTGCG CAACGTTGTT GCCATTGCTG
6301 CAGGCATCGT GGTGTCACGC TCGTCGTTTG GTATGGCTTC ATTCAGCTCC
6351 GGTTCCCAAC GATCAAGGCG AGTTACATGA TCCCCCATGT TGTGCAAAAA
6401 AGCGGTTAGC TCCTTCGGTC CTCCGATCGT TGTCAGAAGT AAGTTGGCCG
6451 CAGTGTTATC ACTCATGGTT ATGGCAGCAC TGCATAATTC TCTTACTGTC
6501 ATGCCATCCG TAAGATGCTT TTCTGTGACT GGTGAGTACT CAACCAAGTC
6551 ATTCTGAGAA TAGTGTATGC GGCGACCGAG TTGCTCTTGC CCGGCGTCAA
6601 CACGGGATAA TACCGCGCCA CATAGCAGAA CTTTAAAAGT GCTCATCATT
6651 GGAAAACGTT CTTCGGGGCG AAAACTCTCA AGGATCTTAC CGCTGTTGAG
```

FIG. 3f

6701 ATCCAGTTCG ATGTAACCCA CTCGTGCACC CAACTGATCT TCAGCATCTT

6751 TTACTTTCAC CAGCGTTTCT GGGTGAGCAA AAACAGGAAG GCAAAATGCC

6801 GCAAAAAAGG GAATAAGGGC GACACGGAAA TGTTGAATAC TCATACTCTT

6851 CCTTTTTCAA TATTATTGAA GCATTTATCA GGGTTATTGT CTCATGAGCG

6901 GATACATATT TGAATGTATT TAGAAAAATA AACAAATAGG GGTTCCGCGC

6951 ACATTTCCCC GAAAAGTGCC ACCTGACGTC TAAGAAACCA TTATTATCAT

7001 GACATTAACC TATAAAAATA GGCGTATCAC GAGGCCCTTT CGTCTTCAA

FIG. 3g

```
        10         20         30         40         50
         |          |          |          |          |
   1 AAGCTTCACG CTGCCGCAAG CACTCAGGGC GCAAGGGCTG CTAAAGGAAG
  51 CGGAACACGT AGAAAGCCAG TCCGCAGAAA CGGTGCTGAC CCCGGATGAA
 101 TGTCAGCTAC TGGGCTATCT GGACAAGGGA AAACGCAAGC GCAAAGAGAA
 151 AGCAGGTAGC TTGCAGTGGG CTTACATGGC GATAGCTAGA CTGGGCGGTT
 201 TTATGGACAG CAAGCGAACC GGAATTGCCA GCTGGGGCGC CCTCTGGTAA
 251 GGTTGGGAAG CCCTGCAAAG TAAACTGGAT GGCTTTCTTG CCGCCAAGGA
 301 TCTGATGGCG CAGGGGATCA AGATCTGATC AAGAGACAGG ATGAGGATCG
 351 TTTCGCATGA TTGAACAAGA TGGATTGCAC GCAGGTTCTC CGGCCGCTTG
 401 GGTGGAGAGG CTATTCGGCT ATGACTGGGC ACAACAGACA ATCGGCTGCT
 451 CTGATGCCGC CGTGTTCCGG CTGTCAGCGC AGGGGCGCCC GGTTCTTTTT
 501 GTCAAGACCG ACCTGTCCGG TGCCCTGAAT GAACTGCAGG ACGAGGCAGC
 551 GCGGCTATCG TGGCTGGCCA CGACGGGCGT TCCTTGCGCA GCTGTGCTCG
 601 ACGTTGTCAC TGAAGCGGGA AGGGACTGGC TGCTATTGGG CGAAGTGCCG
 651 GGGCAGGATC TCCTGTCATC TCACCTTGCT CCTGCCGAGA AAGTATCCAT
 701 CATGGCTGAT GCAATGCGGC GGCTGCATAC GCTTGATCCG GCTACCTGCC
 751 CATTCGACCA CCAAGCGAAA CATCGCATCG AGCGAGCACG TACTCGGATG
 801 GAAGCCGGTC TTGTCGATCA GGATGATCTG GACGAAGAGC ATCAGGGGCT
 851 CGCGCCAGCC GAACTGTTCG CCAGGCTCAA GGCGCGCATG CCCGACGGCG
 901 AGGATCTCGT CGTGACCCAT GGCGATGCCT GCTTGCCGAA TATCATGGTG
 951 GAAAATGGCC GCTTTTCTGG ATTCATCGAC TGTGGCCGGC TGGGTGTGGC
1001 GGACCGCTAT CAGGACATAG CGTTGGCTAC CCGTGATATT GCTGAAGAGC
1051 TTGGCGGCGA ATGGGCTGAC CGCTTCCTCG TGCTTTACGG TATCGCCGCT
1101 CCCGATTCGC AGCGCATCGC CTTCTATCGC CTTCTTGACG AGTTCTTCTG
1151 AGCGGGACTC TGGGGTTCGA AATGACCGAC CAAGCGACGC CCAACCTGCC
```

FIG. 4b

```
1201 ATCACGAGAT TTCGATTCCA CCGCCGCCTT CTATGAAAGG TTGGGCTTCG
1251 GAATCGTTTT CCGGGACGCC GGCTGGATGA TCCTCCAGCG CGGGGATCTC
1301 ATGCTGGAGT TCTTCGCCCA CCCCGGGCTC GATCCCCTCG CGAGTTGGTT
1351 CAGCTGCTGC CTGAGGCTGG ACGACCTCGC GGAGTTCTAC CGGCAGTGCA
1401 AATCCGTCGG CATCCAGGAA ACCAGCAGCG GCTATCCGCG CATCCATGCC
1451 CCCGAACTGC AGGAGTGGGG AGGCACGATG GCCGCTTTGG TCGACAATTC
1501 GCGCTAACTT ACATTAATTG CGTTGCGCTC ACTGCCCGCT TTCCAGTCGG
1551 GAAACCTGTC GTGCCAGCTG CATTAATGAA TCGGCCAACG CGCGGGGAGA
1601 GGCGGTTTGC GTATTGGGCG CCAGGGTGGT TTTTCTTTTC ACCAGTGAGA
1651 CGGGCAACAG CTGATTGCCC TTCACCGCCT GGCCCTGAGA GAGTTGCAGC
1701 AAGCGGTCCA CGCTGGTTTG CCCCAGCAGG CGAAAATCCT GTTTGATGGT
1751 GGTTAACGGC GGGATATAAC ATGAGCTGTC TTCGGTATCG TCGTATCCCA
1801 CTACCGAGAT ATCCGCACCA ACGCGCAGCC CGGACTCGGT AATGGCGCGC
1851 ATTGCGCCCA GCGCCATCTG ATCGTTGGCA ACCAGCATCG CAGTGGGAAC
1901 GATGCCCTCA TTCAGCATTT GCATGGTTTG TTGAAAACCG ACATGGCAC
1951 TCCAGTCGCC TTCCCGTTCC GCTATCGGCT GAATTTGATT GCGAGTGAGA
2001 TATTTATGCC AGCCAGCCAG ACGCAGACGC GCCGAGACAG AACTTAATGG
2051 GCCCGCTAAC AGCGCGATTT GCTGGTGACC CAATGCGACC AGATGCTCCA
2101 CGCCCAGTCG CGTACCGTCT TCATGGGAGA AAATAATACT GTTGATGGGT
2151 GTCTGGTCAG AGACATCAAG AAATAACGCC GGAACATTAG TGCAGGCAGC
2201 TTCCACAGCA ATGGCATCCT GGTCATCCAG CGGATAGTTA ATGATCAGCC
2251 CACTGACGCG TTGCGCGAGA AGATTGTGCA CCGCCGCTTT ACAGGCTTCG
2301 ACGCCGCTTC GTTCTACCAT CGACACCACC ACGCTGGCAC CCAGTTGATC
2351 GGCGCGAGAT TTAATCGCCG CGACAATTTG CGACGGCGCG TGCAGGGCCA
2401 GACTGGAGGT GGCAACGCCA ATCAGCAACG ACTGTTTGCC CGCCAGTTGT
2451 TGTGCCACGC GGTTGGGAAT GTAATTCAGC TCCGCCATCG CCGCTTCCAC
2501 TTTTTCCCGC GTTTTCGCAG AAACGTGGCT GGCCTGGTTC ACCACGCGGG
```

FIG. 4c

```
2551  AAACGGTCTG ATAAGAGACA CCGGCATACT CTGCGACATC GTATAACGTT
2601  ACTGGTTTCA CATTCACCAC CCTGAATTGA CTCTCTTCCG GGCGCTATCA
2651  TGCCATACCG CGAAAGGTTT TGCACCATTC GATGGTGTCA ACGTAAATGC
2701  ATGCCGCTTC GCCTTCGCGC GCGAATTGTC GACCCTGTCC CTCCTGTTCA
2751  GCTACTGACG GGGTGGTGCG TAACGGCAAA AGCACCGCCG ACATCAGCG
2801  CTAGCGGAGT GTATACTGGC TTACTATGTT GGCACTGATG AGGGTGTCAG
2851  TGAAGTGCTT CATGTGGCAG GAGAAAAAG GCTGCACCGG TGCGTCAGCA
2901  GAATATGTGA TACAGGATAT ATTCCGCTTC CTCGCTCACT GACTCGCTAC
2951  GCTCGGTCGT TCGACTGCGG CGAGCGGAAA TGGCTTACGA ACGGGCGGA
3001  GATTTCCTGG AAGATGCCAG GAAGATACTT AACAGGGAAG TGAGAGGGCC
3051  GCGGCAAAGC CGTTTTTCCA TAGGCTCCGC CCCCCTGACA AGCATCACGA
3101  AATCTGACGC TCAAATCAGT GGTGGCGAAA CCCGACAGGA CTATAAAGAT
3151  ACCAGGCGTT TCCCCTGGCG GCTCCCTCGT GCGCTCTCCT GTTCCTGCCT
3201  TTCGGTTTAC CGGTGTCATT CCGCTGTTAT GGCCGCGTTT GTCTCATTCC
3251  ACGCCTGACA CTCAGTTCCG GGTAGGCAGT TCGCTCCAAG CTGGACTGTA
3301  TGCACGAACC CCCCGTTCAG TCCGACCGCT GCGCCTTATC CGGTAACTAT
3351  CGTCTTGAGT CCAACCCGGA AAGACATGCA AAAGCACCAC TGGCAGCAGC
3401  CACTGGTAAT TGATTTAGAG GAGTTAGTCT TGAAGTCATG CGCCGGTTAA
3451  GGCTAAACTG AAAGGACAAG TTTTGGTGAC TGCGCTCCTC CAAGCCAGTT
3501  ACCTCGGTTC AAAGAGTTGG TAGCTCAGAG AACCTTCGAA AAACCGCCCT
3551  GCAAGGCGGT TTTTTCGTTT TCAGAGCAAG AGATTACGCG CAGACCAAAA
3601  CGATCTCAAG AAGATCATCT TATTAATCAG ATAAAATATT TCTAGATTTC
3651  AGTGCAATTT ATCTCTTCAA ATGTAGCACC TGAAGTCAGC CCCATACGAT
3701  ATAAGTTGTT AATTCTCATG TTTGACAGCT TATCATCGAT
```

F I G. 4d

```
         10        20        30        40        50
          |         |         |         |         |
     1  CTCGAGGCAACGCAATTAATGTGAGTTAGCTCACTCATTAGGCACCCCAG
a   51  GCTTTACACTTTATGCTTCCGGCTCGTATGTTGTGTGGAATTGTGAGCGG
   101  ATAACAATTTCACACAGAATTC 10        20        30        40        50
          |         |         |         |         |
     1  CTCGAGGATTCTGAAATGAGCTGTTGACAATTAATCATCGGCTCGTATAA
b   51  TGTGTGGAATTGTGAGCGGATAACAATTTCACACAGAATTC 10        20        30        40        50
          |         |         |         |         |
     1  CTCGAGAAATCATAAAAAATTTATTTGCTTTGTGAGCGGATAACAATTAT
c   51  AATAGATTCAATTGTGAGCGGATAACAATTTCACACAGAATTC 10        20        30        40        50
          |         |         |         |         |
     1  CTCGAGAAAATTTATCAAAAAGAGTGTTGACTTGTGAGCGGATAACAATG
d   51  ATACTTAGATTCATCGAGAGGGACACGGCGAATTC 10        20        30        40        50
          |         |         |         |         |
     1  CTCGAGAAAATTTATCAAAAAGAGTGTTGACTTGTGAGCGGATAACAATT
e   51  ATAATTACAGCCATCGAGAGGGACACGGCGAATTC 10        20        30        40        50
          |         |         |         |         |
     1  CTCGAGAAAATTTATCAAAAAGAGTGTTGACTTGTGAGCGCTCACAATTG
f   51  ATACTTAGATTCATCGAGAGGGACACGGCGAATTC 10        20        30        40        50
          |         |         |         |         |
     1  CTCGAGAATTGTGAGCGGATAACAATTTAGTTGACTTAAAGTCTAACCTA
g   51  TAGGATACTTAGATTCATCGAGAGGGACACGGCGAATTC 10        20        30        40        50
          |         |         |         |         |
     1  CTCGAGAATTGTGAGCGGATAACAATTTAGTTGACTTAAAGTCTAACCTA
h   51  TAGTATAATTAGATTCATCGAGAGGGACACGGCGAATTC
```

FIG. 5a

```
                    10        20        30        40        50
                    |         |         |         |         |
              1  CTCGAGAAAATTTATCAAAAGAGTGTTGACTTGTGAGCGGATAACAATG
i
              51 ATACTTAGATTCAAATTGTGAGCGGATAACAATTTGAATTC 10        20        30        40        50
                    |         |         |         |         |
              1  CTCGAGAAAATTTATCAAAAGAGTGTTGACTTGTGAGCGGATAACAATG
j
              51 ATACTTAGATTCAATTGTGAGCGGATAACAATTTCACACAGAATTC
```

FIG. 5b

1 GAATTCCTCG AGGCTGGCAT CCCTAACATA TCCGAATGGT TACTTAAACA

51 ACGGAGGACT AGCGTATCCC TTCGCATAGG GTTTGAGTTA GATAAAGTAT

101 ATGCTGAACT TTCTTCTTTG CTCAAAGAAT CATAAAAAAT TTA<u>TTTGCTT</u>

151 TCAGGAAAAT TTTTCTG<u>TAT AAT</u>AGATTC<u>A</u> TAAATTTGAG AGAGGAGTTT

201 AAATATGGCT GGTTCTCGCA GAAAGAAACA TATCCATGAA ATCCCGCCTC

251 GAGGAATTC

1   CTCGAGGCTG GCATCCCTAA CATATCCGAA TGGTTACTTA AACAACGGAG

51  GACTAGCGTA TCCCTTCGCA TAGGGTTTGA GTTAGATAAA GTATATGCTG

101 AACTTTCTTC TTTGCTCAAA GAATCATAAA AAATTTAT<u>TT GCTTT</u>CAGGA

151 AAATTTTTCT G<u>TATAAT</u>AGA TTC<u>A</u>AATTGT GAGCGGATAA CAATTTGAAT

201 TC

N25OP29

1   CTCGAGGCTG GCATCCCTAA CATATCCGAA TGGTTACTTA AACAACGGAG

51  GACTAGCGTA TCCCTTCGCA TAGGGTTTGA GTTAGATAAA GTATATGCTG

101 AACTTTCTTC TTTGCTCAAA GAATCATAAA AAATTTAT<u>TT GCTTT</u>CAGGA

151 AAATTTTTCT G<u>TATAAT</u>AGA TTC<u>A</u>ATTGTG AGCGGATAAC AATTTCACAC

201 <u>AGAATTC</u>

FIG. 7

1 CTCGAGGAAC GCCTATCTTA AAGTTTAAAC ATAAAGACCA GACCTAAAGA

51 CCAGACCTAA AGACACTACA TAAAGACCAG ACCTAAAGAC GCCTTGTTGT

101 TAGCCATAAA GTGATAACCT TTAATCATTG TCTTTATTAA TACAACTCAC

151 TATAAGGAGA GACAACTTAA AGAGACTTAA AAGATTAATT TAAAATTTAT

201 CAAAAAGAGT ATTGACTTAA AGTCTAACCT ATAGGATACT TACAGCCATC

251 GAGAGGGACA CGGCGAATAG CCATCCCAAT CGACACCGGG GTCCCTCGAG

301 GCGAATTCCG GATCC

FIG. 8

```
          10        20        30        40        50
          |         |         |         |         |
  1 GTCGACGTTGATCCCCTAGAAATTGTGAGCGCTCACAATTTCTAGGGAAT
 51 TAACGGTACCGAGCTTGTGGCAGTTTAAGGCGGGCGTCCTGCCCGCCACC
101 CTCCGGGCCGTTGCTTCGCAACGTTCAAATCCGCTCCCGGCGGATTTGTC
151 CTACTCAGGAGAGCGTTCACCGACAAACAACAGATAAAACGAAAGGCCCA
201 GTCTTTCGACTGAGCCTTTCGTTTTATTTGATGCCTCAAGCTCGGTACCT
251 CGAGAAAATTTATCAAAAGAGTGTTGACTTGTGAGCGGATAACAATGAT
301 ACTTAGATTCATCGAGAGGGACACGGCGAATTC
```

OP
GATCCCCTAGAAATTGTGAGCGCTCACAATTTCTAGGGAATT

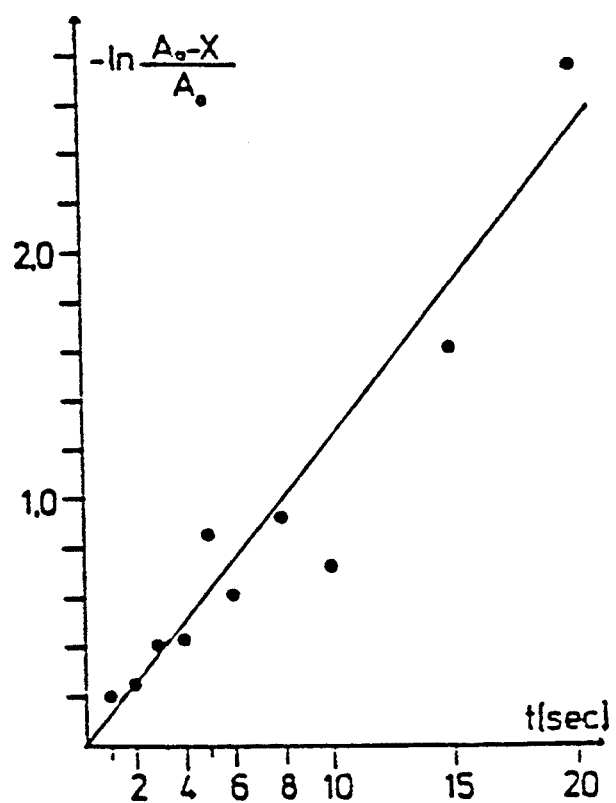
F I G. 16

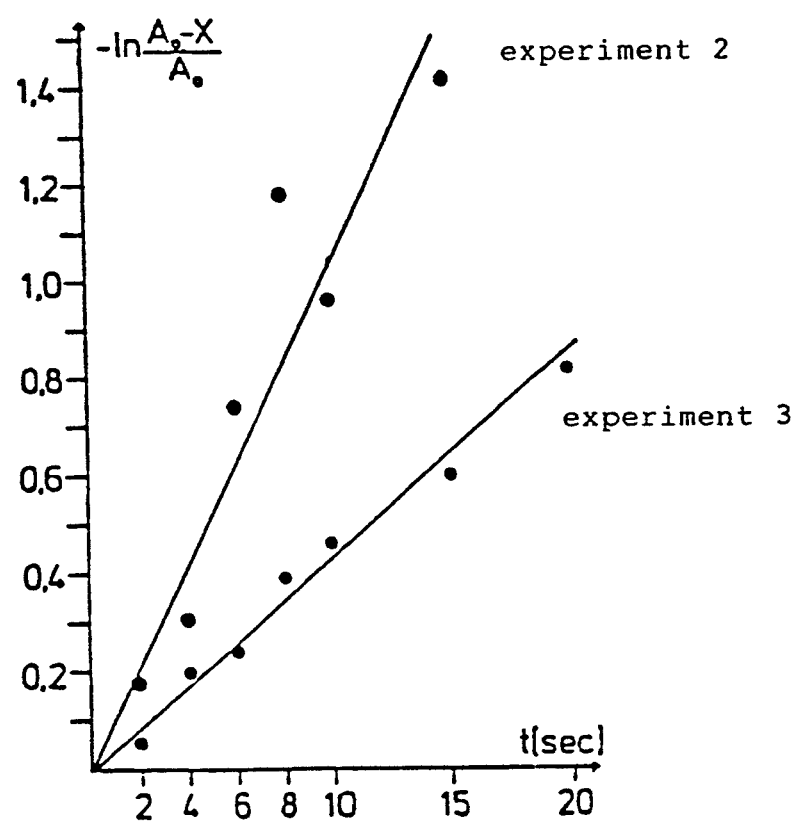
F I G. 18

EXPRESSION CONTROL SEQUENCES

This is a continuation of application Ser. No. 07/223,597 filed Jul. 25, 1988, now abandoned.

TECHNICAL FIELD

The present invention relates to highly efficient and highly repressible expression control sequences, expression vectors which contain these expression control sequences, microorganisms transformed with these expression vectors and methods for their production by means of recombinant DNA technology. The present invention also relates to methods for the production of pro- and eukaryotic proteins using these highly repressible expression control sequences, expression vectors and transformed microorganisms.

BACKGROUND OF THE INVENTION

The level of production of a protein in a host cell is determined by three major factors: the number of copies of its structural gene within the cell, the efficiency with which the structural gene copies are transcribed and the efficiency with which the resulting messenger RNA ("mRNA") is translated. The transcription and translation efficiencies are, in turn, dependent on nucleotide sequences which are normally situated ahead of the desired structural genes or the coded sequence. These nucleotide sequences (expression control sequences) define, inter alia, the location at which the RNA polymerase binds (the promoter sequence to initiate transcription; see also EMBO J. 5, 2995-3000 [1986]) and at which the ribosomes bind and interact with the mRNA (the product of transcription) to initiate translation.

Not all expression control sequences have the same efficiency. It is therefore often advantageous to separate the specific coding sequence for a desired protein from its adjacent nucleotide sequences and to link it with other expression control sequences to achieve a higher expression rate. After this has been accomplished, the newly combined DNA fragment can be inserted into a plasmid having a high copy number or a derivative of a bacteriophage to increase the structural gene copies within the cell, whereby simultaneously the yield of the desired protein can be improved.

Since the overproduction of a normally nontoxic gene product is often harmful to the host cells and lowers the stability of a specific host cell-vector system, an expression control sequence should, in addition to improving the transcription and translation efficiency of a cloned gene, be regulatable to permit the regulation of the expression during the growth of the microorganisms. Some regulatable expression control sequences can be switched off during the growth of the host cells and then can be switched on again at a desired point in time, to favour the expression of large amounts of the desired protein.

Various expression control sequences which fulfill the previously-mentioned conditions have been used for the expression of DNA sequences and genes which code for desired proteins. Such expression control sequences are known, for example, from Science 198, 1056–1063 (1977) (Itakura et al.), Proc. Natl. Acad. Sci. U.S.A. 76, 106–110 (1979) (Goeddel et al.), Nature 283, 171–174 (1980) (Emtage et al.), Science 205, 602–607 (1979) (Martial et al.), Gene 5, 59–76 (1979) (Bernard et al.), Gene 25, 167–178 (1983) (Ammann et al.), Proc. Natl. Acad. Sci. U.S.A., 80, 21–25 (1983) (de Boer et al.) and from European Patent Applications Publication Nos. 41767 and 186069.

SUMMARY OF THE INVENTION

In accordance with the invention it has now been found that highly efficient and highly repressible expression control sequences can be produced by combining promoter sequences having a low signal strength and a high in vivo promoter strength with operator/repressor systems having a high association rate ($K_a$). These expression control sequences are distinguished from the known expression control sequences primarily in that they are more than 1,000-fold repressible and, after induction, bring about a high RNA synthesis rate ($>10$ $P_{bla}$ units) at ideal growth temperatures.

The present invention is therefore concerned with expression control sequences which are characterized by the combination of promoter sequences having a low signal strength and a high in vivo promoter strength with operator/repressor systems having a high association rate, especially those which produce a repression factor of $>1,000$.

BRIEF DESCRIPTION OF THE FIGURES

This invention can be more readily understood by reference to the accompanying Figures, in which the following abbreviations and symbols are used:

B, C, E, H, Ha, K, P, Sa, X and Xb denote cleavage sites for the restriction endonucleases BamHI, ClaI, EcoRI, HindIII, HpaI, KpnI, PstI, SalI, XhoI and XbaI, respectively.  represents the promoters of the genes bla, lacI and neo;  represents the ribosomal binding sites of the genes bla, cat, neo, lacI and lacZ,  represents the terminators $t_o$, T1 and TE, and an arrow indicates the functional orientation of the terminators;  represents the expression control sequences A1OPSA1, lacOP29 and $P_{N25}$;  represents the operator OP in the expression control sequence OPA1OPSA1;  represents the region required for replication (repl.);  represents coding regions for dihydrofolate reductase (dhfr), chloramphenicol acetyltransferase (cat), lac repressor (lacI), β-lactamase (bla), β-galactosidase (lacZ) and neomycin phosphotransferase (neo).

The Figures show the following:

FIGS. 1a–1d

Figure 1A:
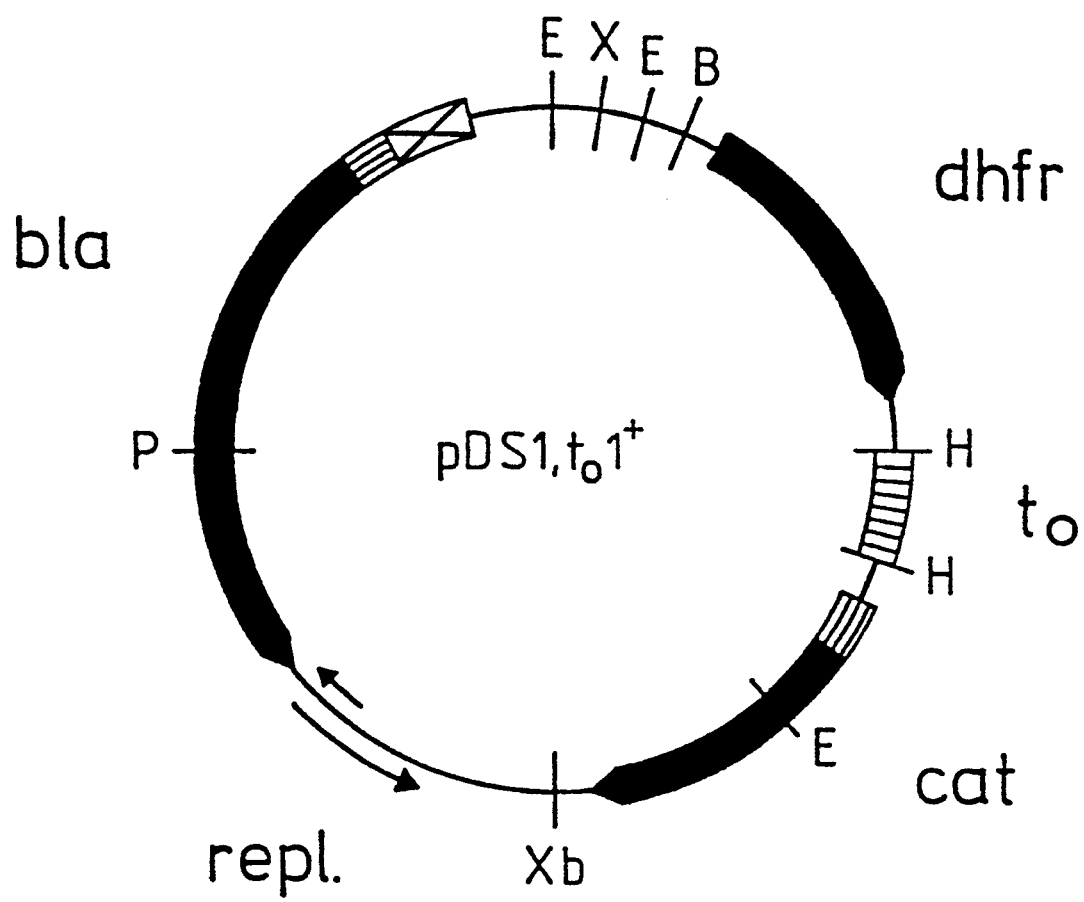

Schematic representation and nucleotide sequence of the plasmid pDS1,tol+. The plasmid is schematically represented in FIG. 1a. In the nucleotide sequence (FIGS. 1b–1d) the recognition sites for the restriction endonucleases given in the schematic representation are overlined, while the regions coding for β-lactamase (bla) and dihydrofolate reductase (dhfr), respectively, are underlined.

FIGS. 2a–2d

Figure 2A:
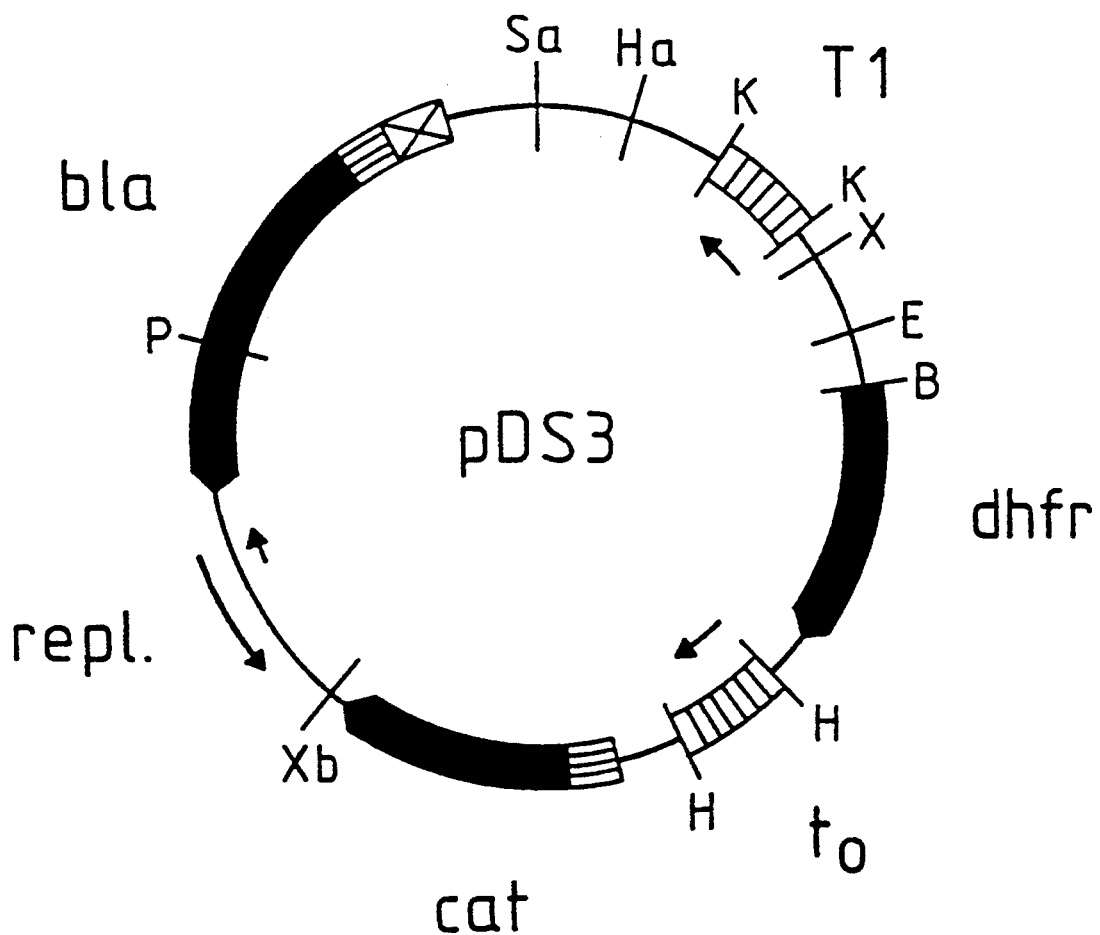

Schematic representation and nucleotide sequence of the plasmid pDS3. The plasmid is schematically represented in FIG. 2a. In the nucleotide sequence (FIGS. 2b–2d) the recognition sites for the restriction endonucleases given in the schematic representation are overlined, while the regions coding for β-lactamase (bla) and dihydrofolate reductase (dhfr), respectively, are underlined.

FIGS. 3a–3g

Figure 3A:
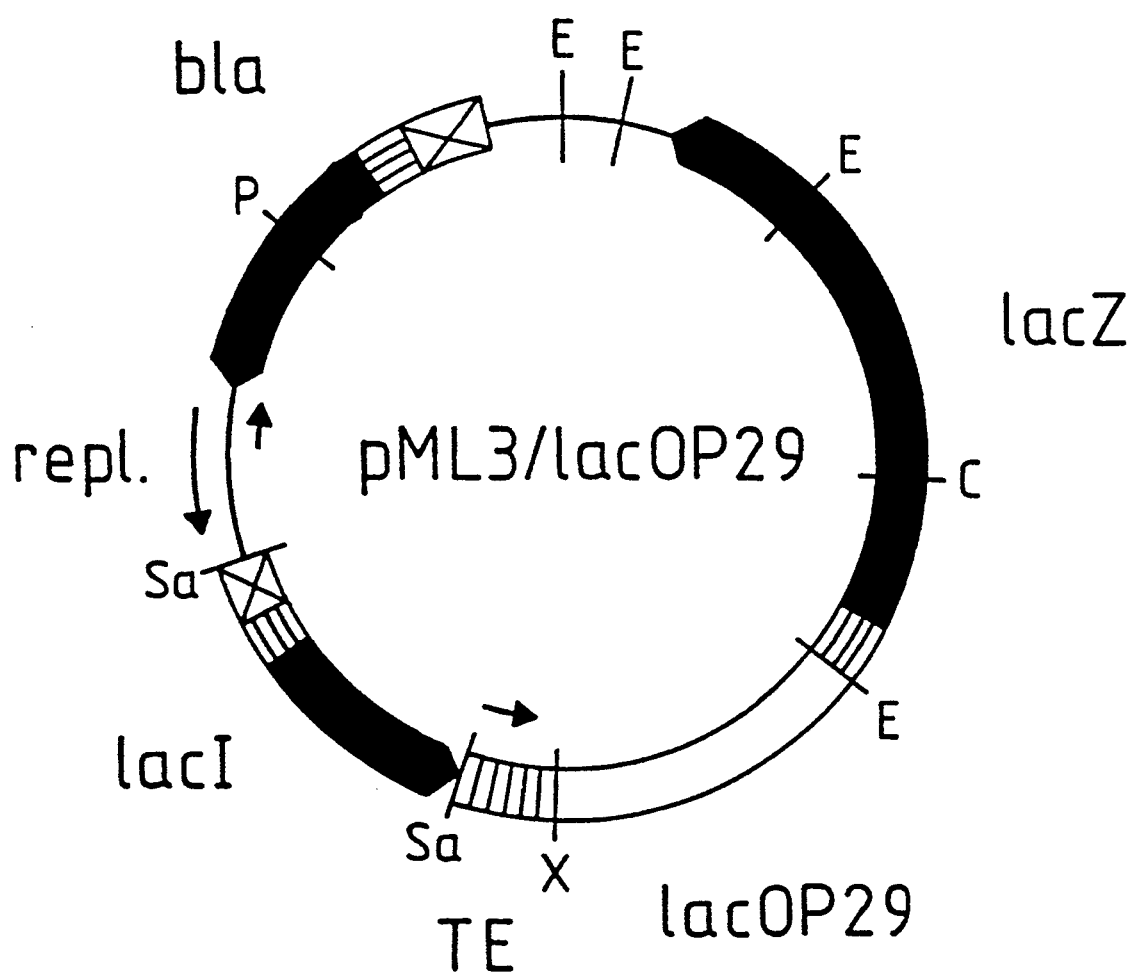

Schematic representation and nucleotide sequence of the plasmid pML3/lacOP29. The plasmid is schematically represented in FIG. 3a. In the nucleotide sequence (FIGS. 3b–3g), which is given as far as it is known, the recognition sites for the restriction endonucleases given in the schematic representation are overlined, while the regions coding for β-lactamase (bla), lac-repressor (lacI) and β-galactosidase (lacZ), respectively, are underlined.

FIGS. 4a–4d

Figure 4A:
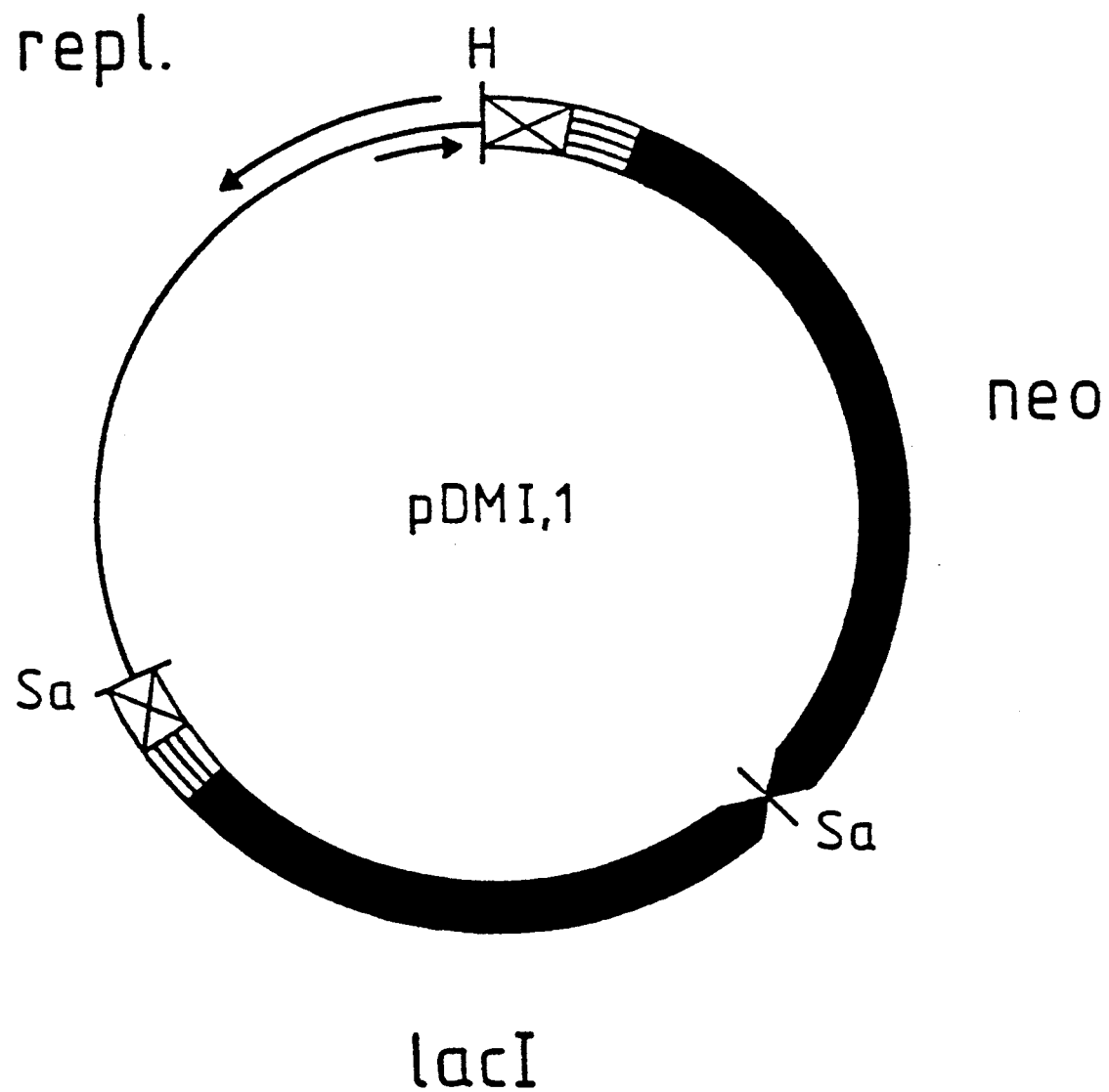

Schematic representation and nucleotide sequence of the plasmid pDMI, 1. The plasmid is schematically represented in FIG. 4a. In the nucleotide sequence (FIGS. 4b–4d) the recognition sites for the restriction endonucleases given in the schematic representation are overlined, while the regions coding for neomycin phosphotransferase (neo) and lac-repressor (lacI), respectively, are underlined.

FIGS. 5a–5b

Nucleotide sequences of the XhoI-EcoRI fragments having the expression control sequences lacOP29(a), tacOP29(b), N25OPSN25OP29(c), A1OPSA1(d), A1A1pOPSA1(f), OPUA1(g), OPUA1CON(h), A1OP-SA1OP21(i) and A1OPSA1OP29(j), respectively. In these sequences the nucleotide at which RNA synthesis starts (+) and the regions at positions −10 and −35 are underlined, while lac-operator sequences are overlined.

FIG. 6

Nucleotide sequence of the EcoRI fragment having the promoter $P_{N25}$. In the sequence the nucleotide at which the RNA synthesis starts and the regions at positions −10 and −35 are underlined.

FIG. 7

Nucleotide sequences of the XhoI-EcoRI fragments having the expression control sequences N25*/O and N25OP29, respectively. In the sequences each nucleotide at which the RNA synthesis starts and the regions at positions −10 and −35 are underlined, while lac-operator sequences are overlined.

FIG. 8

Nucleotide sequence of the XhoI-EcoRI fragment having the promoter $P_{Al}$. In the sequence the nucleotide at which the RNA synthesis starts (position +1) and the regions around positions −10 and −35 are underlined.

FIG. 9

Nucleotide sequence of the SalI-EcoRI fragment containing the expression control sequence OPA1OP-SA1. In the sequence the nucleotide at which the RNA synthesis starts and the regions around positions −10 and −35 are underlined, while lac-operator sequences are overlined.

FIG. 10

Schematic representation of the plasmid pDS1/$P_{N25}$,tol+. Transcription from the promoter $P_{N25}$ is in the clockwise direction.

FIG. 11

Schematic representation of the construction of the plasmid pDS3/A1OPSA1. Transcription from the expression control sequence A1OPSA1 is in the clockwise direction.

FIG. 12

Schematic representation of the construction of the plasmid pDS3/OPA1OPSA1. The nucleotide sequence of the SalI-EcoRI fragment having the expression control sequence OPA1OPSA1, from which transcription is in the clockwise direction, is given in FIG. 9.

FIG. 13

Schematic representation of the construction of the plasmid pML3/A1OPSA1. In this construction the XhoI-EcoRI fragment of the plasmid pML3/lacOP29 containing the expression control sequence lacOP29 was replaced by the corresponding XhoI-EcoRI fragment containing the expression control sequence A1OPSA1.

FIG. 14

Schematic representation of the construction of the plasmid pML3/OPA1OPSA1. Three DNA fragments were used for the construction of this plasmid: the SalI-EcoRI fragment from PDS3/OPA1OPSA1 containing the expression control sequence OPA1OPSA1, the EcoRI-ClaI fragment from pML3/lacOP29 containing parts of the lacZ gene and the larger ClaI-XhoI fragment from pML3/lacOP29. In this construction cleavage sites for SalI and XhoI were linked with each other, whereby both cleavage sites were destroyed.

FIG. 15

Time-dependent course of the complex formation of RNAP and promoter $P_{N25}$ at a concentration of active RNAP of 0.42 nM and a promoter concentration of 0.02 nM.

FIG. 16

Graphical representation of the expression $-\ln[(A_o-X)/A_o]$ as a function of the reaction time at a concentration of active RNAP of 0.42 nM and a concentration of promoter $P_{N25}$ of 0.02 nM.

FIG. 17

Graphical representation of the time-dependent course of the complex formation of RNAP and promoter $P_{N25}$ at a promoter concentration of 0.02 nM and a concentration of active RNAP of 0.32 nM (experiment 2) and 0.15 nM (experiment 3).

FIG. 18

Graphical representation of the expression $-\ln[(A_o-X)/A_o]$ as a function of the reaction time at a promoter concentration of 0.02 nM and a concentration of active RNAP of 0.32 nM (experiment 2) and 0.15 nM (experiment 3).

FIG. 19

Determination of the complex formation rate for promoter $P_{Al}$ with promoter $P_{N25}$ as the internal standard: $-\ln[(B_o-Y)/B_o]$ plotted against $-\ln[(A_o-X)/A_o]$.

FIG. 20

Determination of the complex formation rate for the expression control sequence A1OPSA1 with promoter $P_{Al}$ as the internal standard: $-\ln[(B_o-Y)/B_o]$ plotted against $-\ln[(A_o-X)/A_o]$.

FIG. 21

Determination of the factor for the conversion of β-galactosidase units into $P_{bla}$ units: β-galactosidase units under control of the expression control sequences tacOP29, N25OP29, OPUA1 and OPUA1CON plotted against the corresponding $P_{bla}$ units.

DESCRIPTION OF THE INVENTION

The signal strengths of promoters are specified by the $K_a$ between promoter and RNA polymerase. The signal strengths of the promoter sequences used in this invention have $K_a$ values of about $1 \times 10^6$ to $1.5 \times 10^8$ M$^{-1}$ sec$^{-1}$, with a preferred $K_a$ value of $6 \times 10^7$ M$^{-1}$ sec$^{-1}$. The $K_a$ values are determined as described in Example 3.

The in vivo promoter strength is defined by the RNA synthesis rate, which is mediated by an individual promoter sequence, and is measured in $P_{bla}$ units (Deuschle et al., EMBO J. 5, 2987–2994 [1986]). High in vivo promoter strengths produce RNA synthesis rates of 10–100, preferably more than 20, $P_{bla}$ units.

The $K_a$ of operator/repressor systems describes the velocity with which a repressor binds to the operator. The operator/repressor systems used in this invention have $K_a$ values of about $1 \times 10^8$ to $1 \times 10^{11}$ M$^{-1}$ sec$^{-1}$. The $K_a$ value of $2 \times 10^9$M$^{-1}$ sec$^{-1}$ described for the lac-operator/repressor system (Biochemistry 25, 3845-3852 [1986]) is especially preferred.

Promoter sequences which can be used in this invention include natural promoter sequences and functional variants, which have been specifically altered by mutation or synthesis, and combinations of these promoter sequences. They can be obtained from gram-negative organisms such as E. coli, from gram-positive organisms such as B. subtilis and B. stearothermophilis and from the corresponding phages. Preferred promoter sequences are those from T-coliphages. The T7A1 promoter [the nucleotide sequence of which is shown in FIG. 8 and which is also denoted hereinafter as the A1 promoter ($P_{A1}$)] is especially preferred.

Operator/repressor systems that can be used include all systems that are directly inducible by chemical inducers which produce, in the natural state or after corresponding variations (e.g., by mutation), a repression factor of >1,000. Directly inducible systems that are not part of this invention include systems which are inducible by SOS function (lexA/recA system) or by temperature, such as the $P_L$ operator/repressor system.

Examples of systems which are directly regulatable by chemical induction include, e.g., the regulation units of the lactose, galactose, tryptophan and tetracycline operons, and other negatively controllable operons (i.e., operons which are regulatable by an operator/repressor action; see Miller et al. "The operon", Cold Spring Harbor Laboratory, 1980 and Hillen et al., J. Mol. Biol. 172, 185-201 [1984]).

Especially preferred operator/repressor systems are the natural lac-operator/repressor system (Miller et al., supra) and variants of the above-named operator/repressor systems, which are specifically modified by mutation or synthesis to produce a repression factor of >1,000. The term "repression factor" describes the quotient of the in vivo promoter strengths in the presence and absence of an inducer.

The production of the expression control sequences of the invention can be carried out using recombinant DNA technology methods which are well known in the art (see, e.g., Maniatis et al., "Molecular Cloning", Cold Spring Harbor Laboratory, 1982).

The promoter sequences having a low signal strength and a high in vivo promoter strength can be fused with one or more operator/repressor system(s) to produce the desired expression control sequences. When a single operator/repressor system is used, it can be located within or outside the promoter sequence. Consequently, the operator/repressor system can be integrated into the promoter sequence, can partially replace, precede or succeed it in various positions. Preferably, an operator/repressor system is integrated into the promoter sequence. An especially preferred integration position is in the spacer region between position −12 and −29 (nomenclature as in FIG. 8).

When two operator/repressor systems are used, both can be located within or outside the promoter sequence, or one can be situated within and the other can be situated outside the promoter sequence. Preferably, one is integrated into the spacer region and the other is integrated upstream in the 5'-position, so that by repressor binding a maximal cooperativity is produced between the two operator sequences of the operator/repressor systems. Through such cooperativity, a repression factor up to approximately 30,000 can be obtained.

The preferred expression control sequences of the present invention have been obtained by chemical DNA synthesis, whereby functional parts of the lac-operator sequence have been combined with functional parts the T7A1 promoter sequence. The construction of preferred expression control sequences A1OPSA1, A1OPSA1OP21, A1OPSA1OP29, A1OPSA1 and OPA1OPSA1 is described in detail in Example 2 below. The nucleotide sequences of these expression control sequences are shown in FIGS. 5 and 9, respectively, and the characterizing properties are compiled in Table 8.

The previously mentioned lac-operator sequences are negatively regulated by the lac-repressor. To obtain sufficient amounts of repressor molecules within the cell, the corresponding gene can be expressed in excess in a vector or the chromosome of a bacterium by known methods, such as by integration of the lacI$^q$ gene (Miller et al., supra; Calos, Nature 274, 762-765 [1978].

The expression control sequences of the invention can be inserted using standard procedures into any suitable expression vector which can replicate in gram-negative and/or gram-positive bacteria. Suitable vectors can be constructed from segments-of chromosomal, nonchromosomal and synthetic DNA sequences, such as various known plasmid and phage DNA's (Maniatis et al., supra). Especially suitable vectors are plasmids of the pDS family (Bujard et al., Methods in Enzymology, eds. Wu and Grossmann, Academic Press, Inc., Vol. 155, 416-433 [1987]).

The expression control sequences can also be inserted into the chromosome of gram-negative and gram-positive bacterial cells. In that case, selection agents such as antibiotics, which are generally required when working with vectors, can be dispensed with.

Suitable DNA sequences which can be expressed using the expression control sequences of the invention include those which code in vivo or in vitro for pro- or eukaryotic proteins. For example, such DNA sequences can code for enzymes, hormones, proteins having immunoregulatory, antiviral or antitumour activity, antibodies, antigens and other useful pro- or eukaryotic proteins.

Proteins which can be produced using the expression control sequences of the invention include, for example, malaria surface antigens such as the 5.1 surface antigen, the CS protein and the p190 protein of Plasmodium falciparum, lymphokines, interferons, insulin and insulin precursors, HIV-1 and 2 envelope and structural proteins, growth hormones and growth hormone releasing factors.

Methods for expression of the DNA sequences are well known in the art and are described in Maniatis et al., supra.

In one embodiment of the invention, a desired protein is produced by a method comprising:
(a) transforming a suitable bacterium such as E. coli, Salmonella typhimurium or B. subtilis, with an expression vector in which DNA which codes for a desired pro- or eukaryotic protein is operably linked to an aforementioned expression control sequence;
(b) culturing the transformed bacterium under suitable growth conditions; and
(c) isolating the desired protein from the culture.

In another embodiment of the invention, a desired protein is produced by a method comprising:
(a) inserting an aforementioned expression control sequence, which is operably linked to the coding sequence of a desired pro- or eukaryotic protein, into the chromosome of a suitable bacterium;
(b) cultivating of the thus-obtained bacterium under suitable growth conditions; and
(c) isolating the desired protein from the culture.

The selection of a suitable host organism is determined by various factors which are well known in the art. Factors to be considered include, for example, compatibility with the selected vector, toxicity of the expression product, expression characteristics, necessary biological safety precautions and costs.

Suitable host organisms include gram-negative and gram-positive bacteria, such as *E. coli, Salmonella typhimurium*, and *B. subtilis* strains. *E. coli* strain M15 is especially preferred. Other *E. coli* strains that can be used include other generally available strains such as *E. coli* 294 (ATCC No. 31446), *E. coli* RR1 (ATCC No. 31343) and *E. coli* W3110 (ATCC No. 27325).

EXAMPLES

This invention can be illustrated by the following, nonlimiting Examples.

Example 1

Description of the Plasmids Used

A. Principles

The plasmids pDS1,$t_o$1+ (FIG. 1), pDS3 (FIG. 2), pML3/lacOP29 (FIG. 3) and pDMI,1 (FIG. 4) were used for the production and characterization of the properties of the expression control sequences. *E. coli* cells transformed with these plasmids have been deposited under the Budapest treaty at the Deutschen Sammlung von Mikroorganismen (DSM) in Götingen and assigned the following accession Nos.: *E. coli* M15 (pDS1,$t_o$1+), DSM No. 3135; *E. coli* M15 (pDS5/RBSII, 3A+5A; pDMI,1), DSM No. 3517; *E. coli* M15 (pDS3), DSM No. 4198; and *E. coli* M15 (pML3/lacOP29), DSM No. 4199.

B. Plasmid pDS1,$t_o$1+

The part of pDS1,$t_o$1+ (FIG. 1) which lies between the cleavage site for the restriction endonucleases XbaI and EcoRI and the replication region and the gene for β-lactamase, which confers ampicillin resistance to the cells, is derived from plasmid pBR322 (Bolivar et al., Gene 2, 95-113 [1977]; Sutcliffe, Cold Spring Harbor Symp. Quant. Biol. 43, 77-90 [1979]). The remaining part of the plasmid carries cleavage sites for the restriction endonucleases XhoI, EcoRI and BamHI followed by the gene of the dihydrofolate reductase of the mouse cell line AT-3000 (Chang et al., Nature 275, 617-624 [1978]; Masters et al., Gene 21, 59-63 [1983]), the terminator $t_o$ of the *E. coli* phage lambda (Schwarz et al., Nature 272, 410-414 [1978] and the promoter-free gene of chloramphenicol acetyltransferase (Marcoli et al., FEBS Letters, 110, 11-14 [1980]).

C. Plasmid pDS3

Plasmid pDS3 (FIG. 2) differs from plasmid pDS1,$t_o$1+ on the one hand in a region which carries, besides cleavage sites for various restriction endonucleases, the terminator T1 of the *E. coli* rrnB operon (Brosius et al., J. Mol. Biol. 148, 107-127 [1981]) and on the other hand by the absence of the cleavage site for the restriction endonuclease EcoRI in the gene for chloramphenicol acetyltransferase.

D. Plasmid pML3/lacOP29

The part of pML3/lacOP29 (FIG. 3) which lies between the cleavage sites for the restriction endonucleases SalI and EcoRI and the replication region and the gene for β-lactamase is derived from plasmid pBR322 (Bolivar et al., supra; Sutcliffe, supra). The remaining part of the plasmid carries, in addition to the complete lac I gene (Farabough, Nature 274, 765-769 [1978]), which codes the lac-repressor, the terminator $T_E$ of the *E. coli* phage T7 (Dunn et al., J. Mol. Biol., 166, 477-535 [1983]), the expression control sequence lacOP29 (see Example 2) and the promoter-free gene for β-galactosidase (Kalnins et al., EMBO J. 2, 593-597 [1983]).

E. Plasmid pDMI,1

Plasmid pDMI,1 (FIG. 4) carries the gene of neomycin phosphotransferase from the transposon Tn5 (Beck et al., Gene 19, 327-336 [1982]), which confers kanamycin resistance to the *E. coli* cells, and the lac I gene (Farabough, supra) having the promoter mutation I$^q$ (Calos, Nature 274, 762-765 [1978]), which codes for the lac-repressor. Moreover, plasmid pDMI,1 contains a region of plasmid pACYC184 (Chang et al., J. Bacteriol. 134, 1141-1156 [1978]) which contains all information required for the replication and stable transmission to the daughter cells. Plasmid pDMI,1 is compatible with the above-described plasmids and their derivatives.

Example 2

Production and Cloning of the Expression Control Sequences

A. Principles

After the production of the expression control sequences they were integrated into suitable plasmids for the characterization of their properties.

B. Production of the Expression Control Sequences

1. Expression Control Sequences lacOP29, tacOP29, A1OPBCONA1, OPUA1, OPUA1CON, N25OPSN-25OP29, $P_{A1}$, A1OPSA1, A1pOPSA1, A1OPSA1OP21 and A1OPBA1OP29.

For the production of these expression control sequences, single-stranded DNA fragments were first synthesized chemically (Bannwarth et al., DNA 5, 413-419 [1986]). These fragments were then hybridized and ligated as described by Maniatis et al., supra. The sequences of the thus-obtained double-stranded XhoI-EcoRI fragments having the corresponding expression control sequences are given in FIGS. 5 and 8, respectively.

2. Expression Control Sequences $P_{N25}$, N25*/O and N25OP29

The expression control sequences $P_{N25}$, N25*//O and N25OP29 (FIG. 6 and FIG. 7) can be produced as described in the above paragraph.

3. The Expression Control Sequence OPA1OPSA1

The sequence of the expression control sequence OPA1OPSA1 is represented in FIG. 9. Its production is described in paragraph D.

C. Integration of Promotor $P_{N25}$ Into Plasmid pDS1, $t_o$1+

Figure 10:
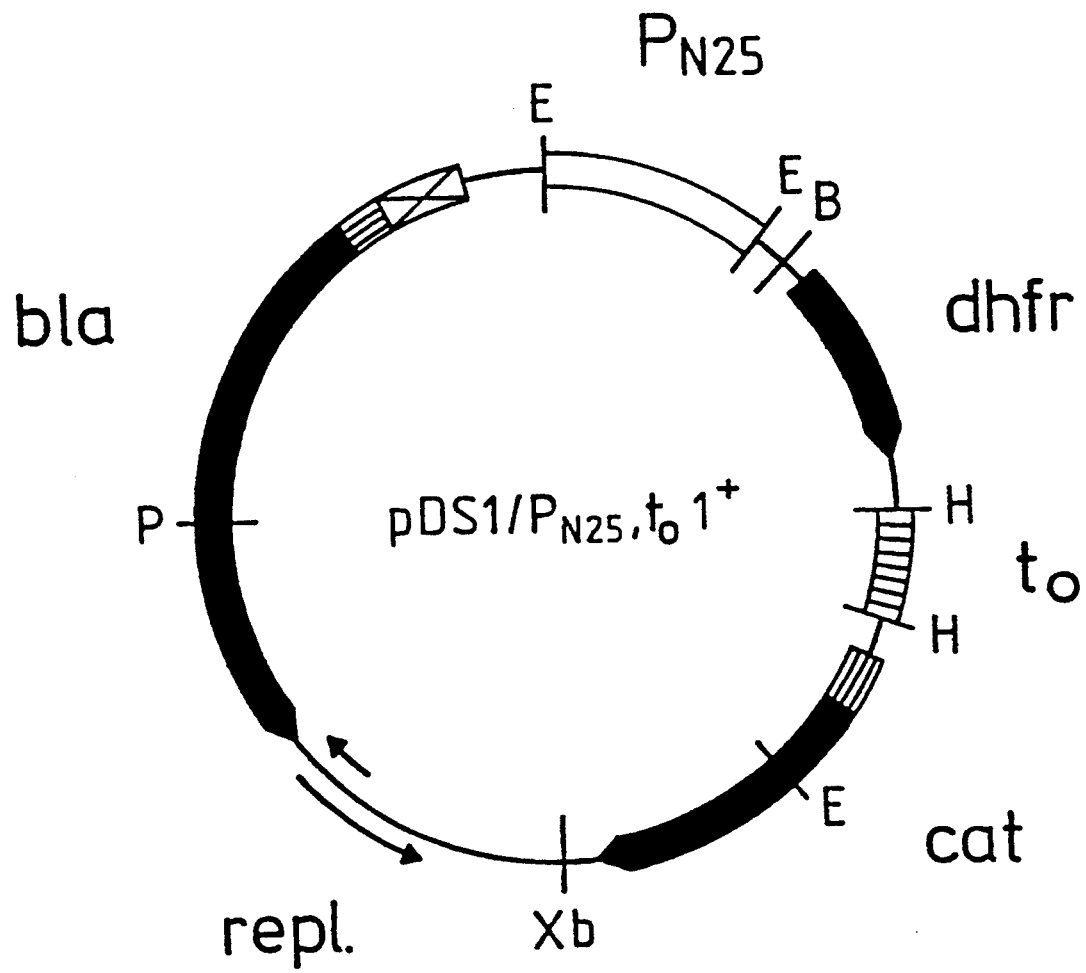

Promoter $P_{N25}$ was integrated into plasmid pDS1,$t_o$1+ (FIG. 1) as part of an EcoRI fragment (see FIG. 6) according to methods described by Maniatis et al., supra, whereby plasmid pDS1/$P_{N25}$,$t_o$1+ (FIG. 10)

was obtained. This plasmid was used as a source for the production of promoter $P_{N25}$ in larger amounts.

D. Integration of the Expression Control Sequences Into Plasmid pDS3

The expression control sequences lacOP29, tacOP29, OPUA1, OPUA1CON, $P_{N25}$, N25*/O, N25OP29, N25OPSN25OP29, $P_{A1}$, A1OPSA1, A1OPSA1OP21, A1OPSA1OP29, A1OPSCONA1 and A1pOPSAL were integrated into the plasmid pDS3 (FIG. 2) using methods described by Maniatis et al., supra. One such cloning is schematically represented in FIG. 11, with the expression control sequence A1OPSA1 as an example.

Figure 11:
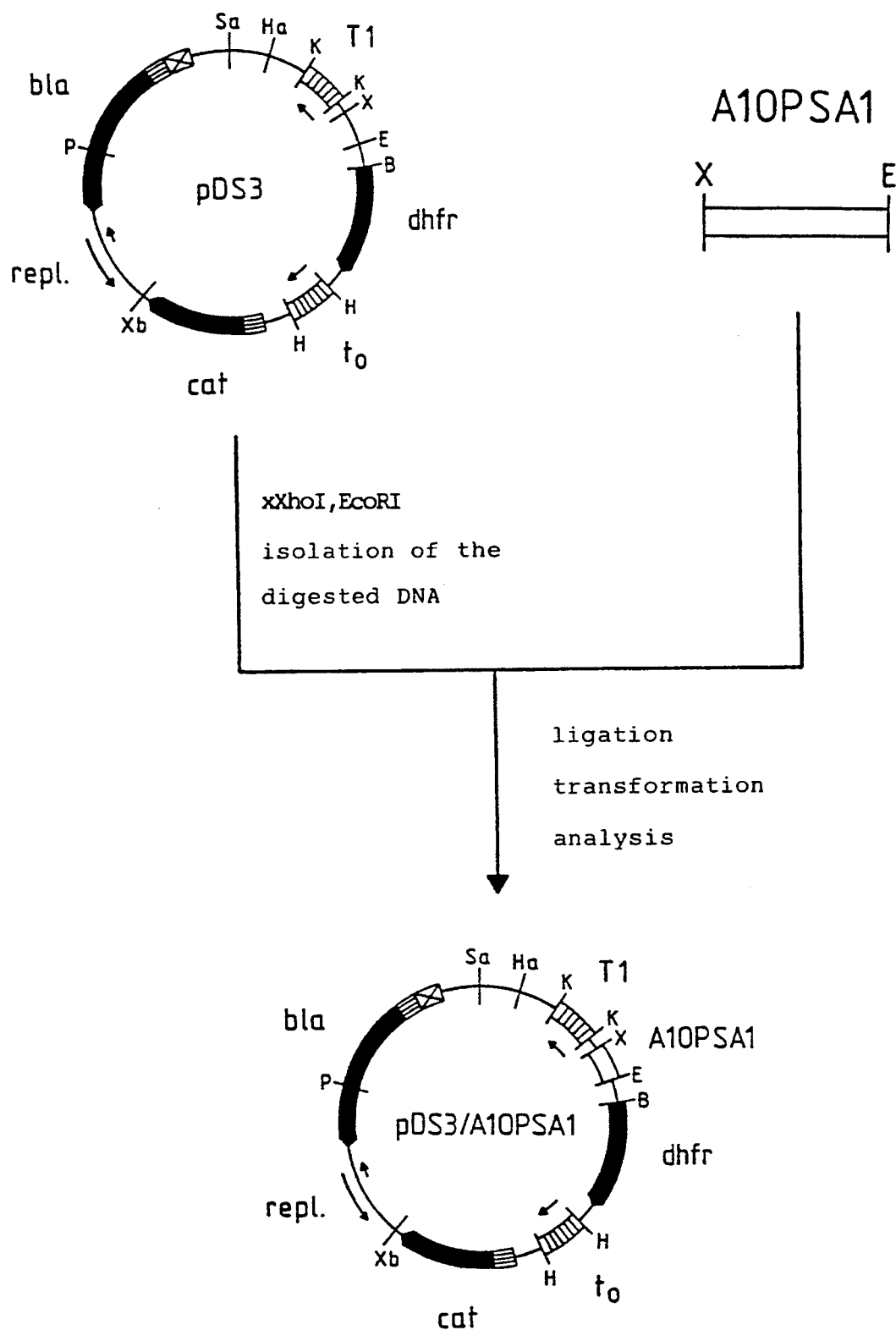
Figure 12:
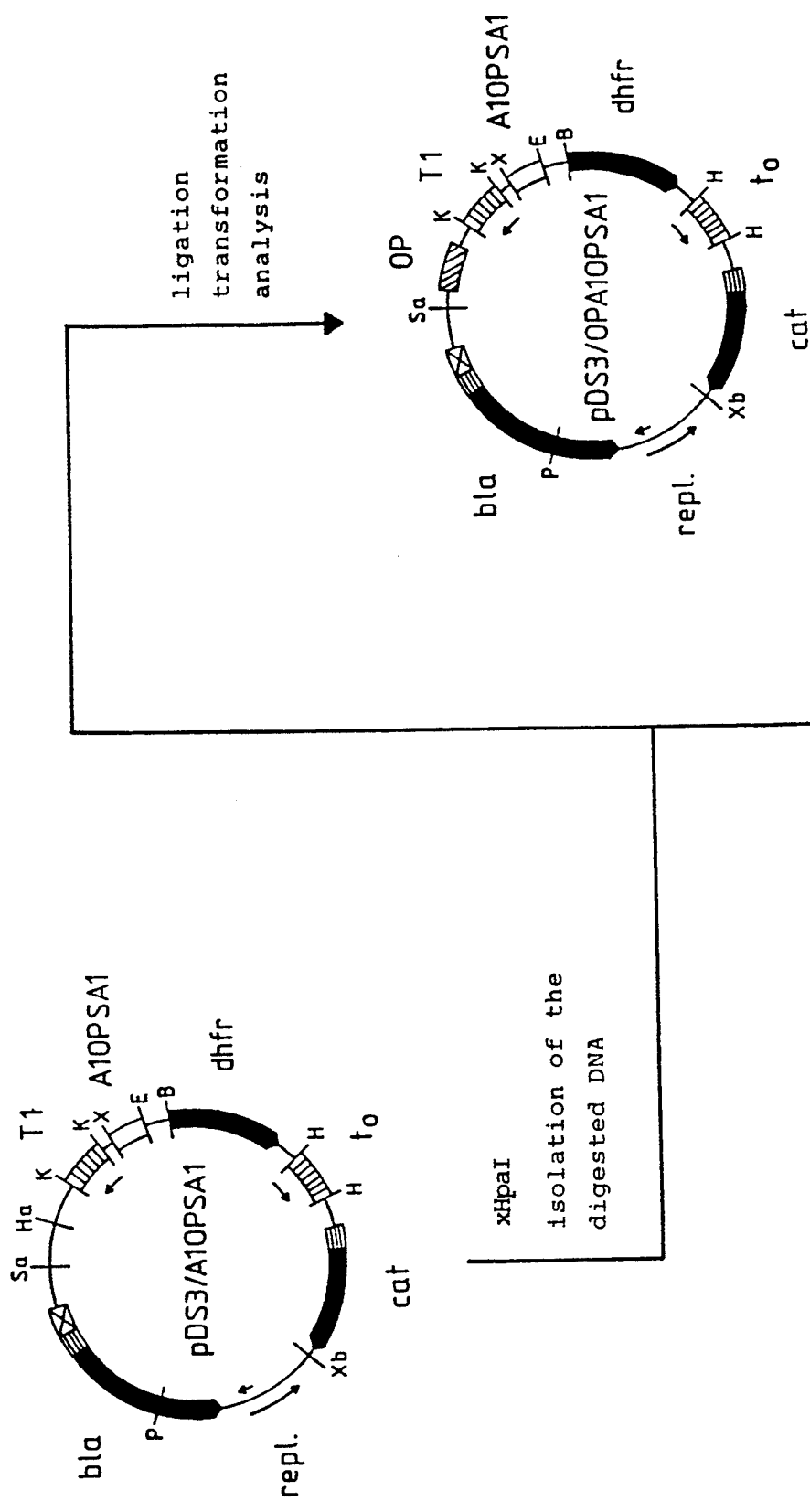

The expression control sequence OPA1OPSA1 was produced (FIG. 12) by integrating a chemically synthesized DNA fragment, which contains a palindromic sequence of the lac-operator, into the HpaI cleavage site of plasmid pDS3/A1OPSA1 (FIG. 11).

The pDS3 derivatives having the corresponding expression control sequences were used both to determine the association rates between promoter and RNAP and to determine the promoter strengths of the individual expression control sequences.

E. Integration of the Expression Control Sequences into Plasmid pML3/lacOP29

Figure 13:
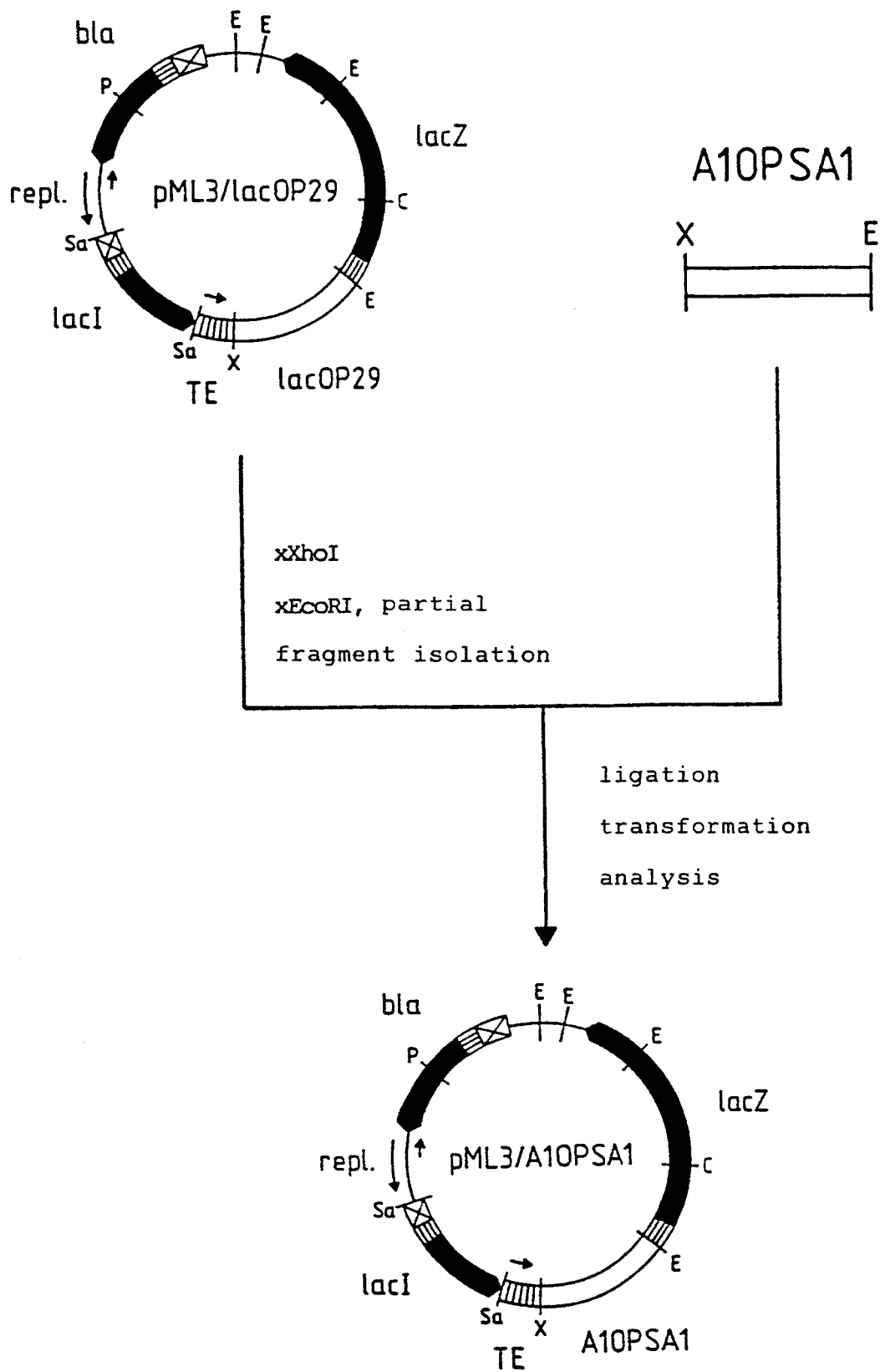

Plasmid pML3/lacOP29 (FIG. 3) carries the expression control sequence lacOP29 between the cleavage sites for the restriction endonucleases XhoI and EcoRI. These plasmids were produced (FIG. 13) according to methods described in the literature (Maniatis et al., supra) in which lacOP29 was replaced in each case by one of the expression control sequences tacOP29, N25OP29, N25OPSN25OP29, A1OPSA1, A1OP-SA1OP21, A1OPSA1OP29, A1OPSCONA1, A1pOPSA 1, OPUA1 and OPUA1CON, respectively.

Figure 14:
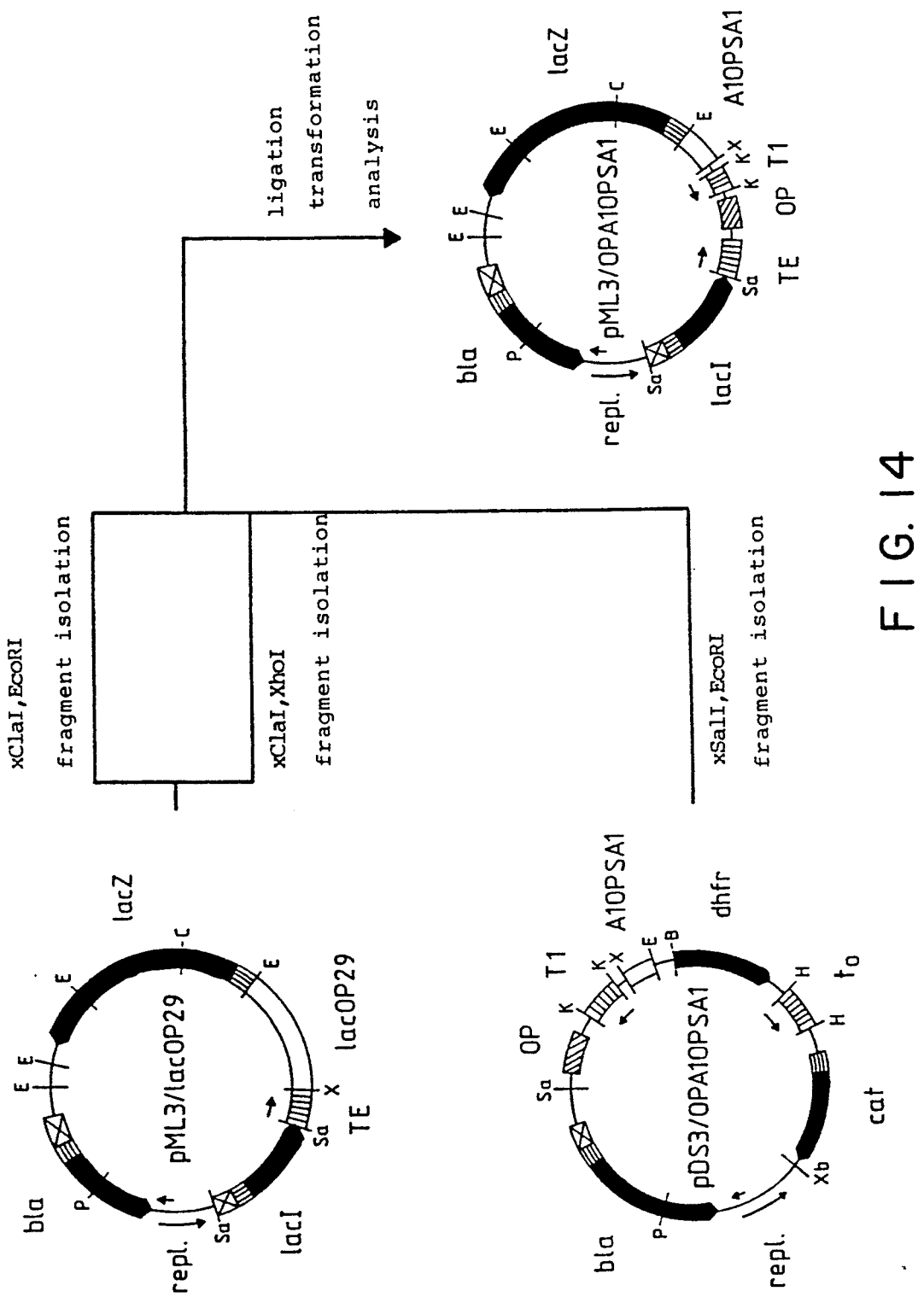

Plasmid pML3/OPA1OPSA1 containing the expression control sequence OPA1OPSA1 was produced as described schematically in FIG. 14.

The pML3 derivatives containing the corresponding expression control sequences were used to determine the in vivo promoter strengths under repressed conditions.

Example 3

Determination of the Signal Strengths

A. Principles

For the determination of the signal strengths of the promoters and promoter/operator elements, the absolute value of the $K_a$ between E. coli RNA polymerase (RNAP) and promoter $P_{N25}$ was first determined. Then, the $K_a$ values for the remaining signals were determined by relative measurements using promoter $P_{N25}$ as an internal standard.

B. Determination of $K_a$ for RNAP and Promoter $P_{N25}$

The $K_a$ for RNAP and promoter $P_{N25}$ was determined by means of filter binding experiments in which the formation of RNAP/promoter complexes as a function of the RNAP concentration and the reaction time were determined quantitatively. Since RNAP and the promoters are biological materials, the evaluation of such experiments presupposed that for both reactants the concentration of the active molecule was known. Thus, e.g., for RNAP the concentration of the active polymerase molecule had to be considered, not the protein concentration. The same was true for promoter $P_{N25}$ and for the single-stranded fd-DNA, which was used as a competitor for nonspecific binding and for the termination of association reactions.

Accordingly, a description of the theoretical derivation of the complex formation rates will be followed below by a detailed explanation of the production and analysis of all reactants, and that will be followed by actual experiments for the determination of $K_a$.

1. Theoretical Derivation of $K_a$

The general reaction scheme is

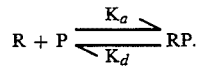

wherein
R represents the free concentration of RNAP,
P represents the free concentration of the promoters,
RP represents the concentration of the RNAP/promoter complexes,
$K_a$ represents the association rate and
$K_d$ represents the dissociation constant.

The following applies to the course of the reaction per unit time:

$$dP/dt = -K_a \times R \times P + K_d \times RP$$

If the half life of the RNAP/promoter complexes is large—i.e., the dissociation constant $K_d$ is small—the term $K_d \times RP$ can be disregarded, and $$dP/dt = -K_a \times R \times P \quad (1)$$

applies to the change in the promoter concentration per unit time.

R and P change with time, but if the RNAP is present in a large excess, its concentration during the course of the reaction can be regarded as being constant (i.e., when R is constant, then dR/dt=0), and $$K_a \times R = m \quad (2)$$

applies.

Therefore, the following equation applies to the change in the promoter concentration per unit time [see equations (1) and (2)]:

$$dP/dt = -m \times P$$

or, $$-dP/P = m \times dt$$

Integration of this equation yields:

$$-\ln P = m \times t \quad (3)$$

Equation (3) corresponds to a reaction equation of the first order, i.e., formally to the "decomposition of free promoter fragment in RNAP/promoter complex", with the velocity constant m [1/sec]. P in this case is the amount of free promoter at time t (for t=0 seconds, P=1). This amount can be determined experimentally (see paragraph 6). Knowing $A_O$ (total amount of promoters) and X (amount of RNAP/promoter complexes at the point in time of the reaction t), the so-called "pseudo first order" constant m can be calculated with the aid of equation (3):

$$P = (A_O - X)/A_O,$$

and the result is $$m = -\ln[(A_O - X)/A_O]/t \quad (4)$$

Since the formation of the promoter/operator complexes is a bimolecular reaction of the second order, the constant m depends on the concentration of the RNAP. If this is known, then $K_a$ in the equations $$m = K_a \times R \quad (2)$$

and $$m = -\ln[(A_O - X)/A_O]/t \quad (4),$$

can be calculated as follows:

$$K_a \times R = -\ln[(A_O - X)/A_O]/t$$

or, $$K_a = -\ln[(A_O - X)/A_O]/(t \times R) \quad (5)$$

In the derivation of $K_a$, it has been assumed that the reverse reaction (i.e., the decomposition of RNAP/promoter complexes), can be disregarded ($K_d \times RP = O$). Such decomposition is a reaction of the first order and is therefore dependent on the concentration of the reactants. On the other hand, the association is concentration-dependent. Accordingly, for the determination of $K_a$ the concentrations of the reactants selected must be sufficiently high that the association process takes place in a period in which the decomposition of complexes can be disregarded. This presupposes knowledge of the stability of the RNAP/promoter complexes.

Furthermore, it has been assumed that during the course of the reaction the concentration of the free RNAP can be regarded as constant. For this purpose, the RNAP must be present in a large excess relative to the promoters. It should also be noted that the RNAP can also bind to nonspecific DNA sequences, but the number of such nonspecific binding sites can be minimized by investigating promoters on small, isolated DNA fragments. With an excess of approximately 10 RNAP molecules per promoter, the concentration of the free RNAP during the course of the reaction can be regarded as constant.

2. Production of the Probe Containing Promotor $P_{N25}$

Plasmid pDS1/$P_{N25}$,$t_o$1+ (FIG. 10) contains promoter $P_{N25}$ on a 254 bp EcoRI fragment (FIG. 6). This plasmid was constructed by integrating the mentioned EcoRI fragment into the EcoRI cleavage site of plasmid pDS1, $t_o$1+ (FIG. 1), which is adjacent to the XhoI cleavage site.

To purify the promoter fragment, plasmid pDS1/$P_{N25}$,$t_o$1+ was first purified (Maniatis et al., supra) and 0.5 mg of this plasmid was then cleaved with the restriction endonuclease EcoRI. After phenol extraction and ethanol precipitation (Maniatis et al., supra), the cleaved DNA was dissolved in TE buffer (10 mM Tris HCl, 1 mM EDTA, pH 7.6) and, after the addition of sample buffer, subjected to electrophoresis in 6% polyacrylamide gels (Maniatis et al., supra). Subsequently, the fragments carrying promoter $P_{N25}$ were cut out from the gel with a scalpel and electrophoresed on DEAE paper (DE 81, Whatman, England). After three-fold washing with ethanol and TE buffer, the paper was dried in air and the DNA was eluted with a buffer containing 10 mM Tris HCl, 1 mM EDTA and 1.5 M NaCl, pH 7.6. After a 1:3 dilution of the resulting DNA solution with TE buffer, the DNA was precipitated with ethanol, the sediment was washed with 80% ethanol and the DNA was dissolved in TE buffer.

The concentration of this DNA solution was determined spectrophotometrically as described by Mahler et al. [J. Mol. Biol. 9, 801–811 (1964)]. A portion of the DNA stock solution was then diluted 1:30 in TE buffer, and the extinction of this dilution was measured against TE buffer as the blank. The following values were obtained:

$\Delta E_{260} = 0.108$ $\Delta E_{280} = 0.058$ $\Delta_{260}/\Delta E_{280} = 1.86$ Using the conversion factor of $\Delta E_{260} = 50$ μg DNA/ml and the dilution factor, a DNA concentration of 162 μg/ml was obtained for the stock solution. This value corresponded to a concentration of 0.96 pMoles DNA fragment/μl, considering the length of the promoter fragment (254 bp). The relationship of the extinctions at 260 and 280 nm permitted assessment of the purity of the DNA solution, with a high purity DNA solution having a $\Delta E_{260}/\Delta E_{180}$ value of 1.86.

The concentration of the DNA solution was also determined by comparing this solution with an RNA-free solution of plasmid pDS1, $t_o$1+ of known concentration ($\Delta E$ measurement). For this purpose, 0.09 pMole portions of the DNA solution containing the promoter fragment were mixed with 0.2, 0.1, 0.5 and 0.025 pMoles of the cleaved pDS1, $t_o$1+ plasmid DNA and characterized in a 6% polyacrylamide gel (Maniatis et al., supra). The pherogram obtained was evaluated densitometrically, whereby a concentration of 0.8 pMoles/μl was obtained for the promoter fragment in comparison to the cleaved pDS1, $t_o$1+ plasmid DNA.

To determine the purity of the promoter fragment, 0.36 pMole of this fragment were firstly characterized in a polyacrylamide gel. After staining with ethidium bromide, no impurities could be detected. Furthermore, the fragment was radioactively labelled with $^{32}P$ (see below) and also characterized electrophoretically. Only the promoter fragment could be detected by autoradiography. It thus was shown that the isolated EcoRI fragment having promoter $P_{N25}$ was not contaminated with substantial amounts of RNA or DNA and was present at a concentration of 0.88±0.08 pMoles/μl.

To determine the concentration of the active polymerase (see below), a mixture of the isolated EcoRI fragment having promoter $P_{N25}$ and the corresponding fragment radioactively labelled with $^{32}P$ was used as the promoter probe. This radioactively labelled DNA was produced as follows: the DNA was first dephosphorylated with the aid of CIP (calf intestinal alkaline phosphatase) (Maniatis et al., supra) and then labelled by the incorporation of $^{32}P$ ($\gamma$-$^{32}P$ ATP, Amersham, 3000 Ci/mMol) with T4-polynucleotide kinase (Maniatis et al., supra). Subsequently, the radioactively labelled EcoRI fragment having promoter $P_{N25}$ was purified by chromatography in Sephadex G75® (Pharmacia, Sweden).

To determine the specific activity of this probe, the radioactivity was measured and the DNA concentration was determined electrophoretically against the pre-treated, isolated EcoRI fragment (see above). Probes having promoter $P_{N25}$ of defined concentration and specific activity were subsequently obtained by mixing the untreated and the radioactively labelled EcoRI fragments.

3. Production and Characterization of Single-stranded M13mp8-DNA

Single-stranded M13mp8-DNA was used both as a competitor for the nonspecific binding of RNAP to DNA and to terminate association reactions. The production and characterization of this DNA is described below. *E. coli* JM 101 cells (Maniatis et al., supra; GIBCO-BRL, Basle) were transformed with 0.01 pMoles of M13mp8 RFI-DNA (Pharmacia, Sweden) according to the method of Morrison [Methods in Enzymology 68, 326–331 (1979)]. The cells were then plated onto indicator plates containing isopropylthiogalactoside (IPTG) and X-gal (5-bromo-4-chloro-3-indolyl-$\beta$-D-galactoside). See Miller, "Experiments in Molecular Genetics", Cold Spring Harbor Laboratory (1972) and Messing et al. Gene 19, 269–276 (1982).

Turbid plaques containing transformed *E. coli* JM 101 cells were taken from the top-agar layer of these indicator plates with a Pasteur pipette, transferred into 10 ml of LB medium and incubated for 8 hours in a shaking incubator (37° C., 220 rpm). Subsequently, the cells were centrifuged and the supernatant containing M13mp8 phage was used for the re-infection of *E. coli* JM 101 cells.

For this purpose, *E. coli* JM 101 cells in 500 ml of M9 minimal medium (Miller, supra) were grown (37° C.; 220 rpm) to an $OD_{600}=2$, and 1 ml of the supernatant containing M13mp8 phage was added to the cells. After incubation at 37° C. for a further 12 hours, the cells were centrifuged. The phage were precipitated from the supernatant with 3% polyethylene glycol (PEG 6000) and 0.5M NaCl and centrifuged. The sediment was resuspended in 20 ml of TE buffer and extracted twice at 65° C. with phenol (equilibrated in 200 mM Tris HCl, pH 8) and phenol/chloroform (1:1).

The thus-liberated single-stranded M13mp8-DNA was precipitated with ethanol and dissolved in 1 ml of TE buffer. The concentration of this DNA solution was determined spectrophotometrically (Mahler et al., supra), using the conversion factor 1 $OD_{260}=36$ $\mu$g of single-stranded DNA/ml.

4. Determination of the Concentration of Active Polymerase in RNAP Solutions.

For the determination of the concentration of active *E. coli* RNA polymerase in RNAP solutions, after incubating the RNAP in the presence of an excess of promoter fragments, the amount of RNAP/promoter complexes formed was determined with the aid of filter-binding experiments. From this amount, the concentration of bound *E. coli* RNA polymerase was calculated relative to the amount of promoter fragments used. The thus-determined concentration of RNAP molecules capable of binding was equivalent to the concentration of free, active RNAP.

One such concentration determination was carried out by incubating 0.12 pMole of promoter fragment (see paragraph B, 2.; specific activity; $4 \times 10^4$ cpm pMol) at 37° C. for 2 minutes in 50 $\mu$l of binding buffer (BB; 20 mM Tris HCl, pH 8.0, 10 mM $MgCl_2$, 0.1 mM EDTA, 1 mM DTT, 5% glycerol, 120 mM KCl). *E. coli* RNAP (Pharmacia, Sweden) was diluted at 0° C. in BB containing 120 mM KCl. One hundred microliters of the diluted RNAP were incubated at 37° C. for 2 minutes and then pipetted into the solution containing the promoter fragment.

The mixture was held at 37° C. for 5 minutes, and 300 $\mu$l of BB containing 0.8 $\mu$g of single-stranded M13mp8-DNA (see paragraph B, 3) which had been preincubated at 37° C. for 2 minutes were added. After incubation at 37° C. for a further 5 minutes, the mixture was filtered at 37° C. through nitrocellulose.

A nitrocellulose filter (nitrocellulose filter BA, 0.45 $\mu$m; Sartorius, Götingen) was cut into small square pieces (4×4 mm) and soaked in BB containing 40 mM KCl. One piece was transferred onto a similarly soaked glass fibre filter (GF/A, Whatman) which was on a glass frit. This glass frit was in a 37° C. water bath and was connected to a water-jet pump. The reaction mixture was filtered with a filtration velocity of 1 ml/minute. Thereafter, the filter was rinsed with 1 ml of BB containing 40 mM KCl (pre-warmed to 37° C.).

To elute the filter-bound DNA, the nitrocellulose filter was squashed into an Eppendorf test tube with a pipette tip (Eppendorf) and, after the addition of 20 $\mu$l of elution buffer (EB) (10 mM Tris HCl, mM EDTA, 0.1% SDS, pH), squeezed out with a pipette tip. The elution batch was placed on ice for 30 minutes and then centrifuged for 55 minutes (Eppendorf bench centrifuge, 12,000 rpm). The elution solution was separated and transferred to another Eppendorf test tube.

The filter was eluted further by adding 50 $\mu$l of TE buffer into the filter, shaking the mixture for 3 minutes (Eppendorf shaker), separating the rinse solution and combining the eluate with the first elution solution. After a total of three elution and rinsing steps, about 95% of the bound DNA was eluted. After removing any possibly present broken filter pieces by centrifugation, the radioactivity of the eluate was measured (210 $\mu$l).

The concentration of active polymerase in a RNAP solution is determined by adding an aliquot of the solution to 0.12 pMoles of promoter fragment. The numerical value thus obtained is compared to the value obtained when a large excess (saturating amount) of active polymerase is added to 0.12 pMoles of promoter fragment. The concentration in the solution can then be calculated using the ratio of the solution value obtained to the value produced with the saturating amount of active polymerase, taking into account any dilutions made in assaying the solution.

5. Determination of the Half Life of RNAP/promoter Complexes

As noted above, in the derivation of $K_a$ it has been assumed that the decomposition of RNAP/promoter complexes during the experimental period can be disregarded. This assumption was checked in experiments in which the half life of RNAP/promoter complexes was determined.

To determine the half life, RNAP/$P_{N25}$ complexes were formed by incubating 0.06 pMoles of promoter fragment (specific activity $2.4 \times 10^6$ cpm/pMol) with 1.2 pMoles of active polymerase in BB containing 120 mM KCl at 37° C. for 5 minutes. After the addition of 5 $\mu$g of single-stranded M13mp8-DNA, samples were removed from the batch, which was held at 37° C., at various times (0–180 minutes) and filtered at 37° C. through a nitrocellulose filter. The filter-bound radioactivity was measured as described above and the values obtained were plotted against the reaction time. Evaluation of this graph showed that under these experimental conditions complexes of RNAP and promoter $P_{N25}$ have a half life of approximately 3 hours.

6. Determination of the $K_a$ for RNAP and Promoter $P_{N25}$

Kinetic measurements for the determination of $K_a$ for RNAP and promoter $P_{N25}$ were carried out under "pseudo first order" conditions, i.e., with a large RNAP excess. The experimental conditions and reaction times were chosen so that the reverse reaction, i.e., the decomposition of formed RNAP/promoter complexes, could be disregarded (duration of the experiment a maximum of 7 minutes with a half life of the complex of approximately 180 minutes). The binding reactions were all carried out according to a uniform scheme, whereby in three independent series of experiments both the reaction volume and the concentration of reactants were varied.

$P_{N25}$ promoter fragments were pre-incubated in buffer before the RNAP solution, which was likewise pre-incubated in buffer and whose concentration of active polymerase was determined in experiments carried out in parallel as described above, was added and the reaction was started by mixing the batches. After selected reaction times (1–120 seconds), reaction was stopped by the addition of single-stranded M13mp8-DNA. The RNAP/promoter complexes formed were then determined quantitatively by filter-binding experiments. Three experiments for the determination of the $K_a$ are described below.

Experiment 1

50 µl of $P_{N25}$ promoter fragment (0.045 nM, specific activity $3 \times 10^6$ cpm/pMol) in BB containing 120 mM KCl were incubated at 37° C. for 2 minutes. RNAP was diluted stepwise (from 1:10 to 1:20) at 0° C. in BB containing 120 mM KCl. Subsequently, 100 µl of a 1:5000 dilution were pre-incubated at 37° C. for 2 minutes (0.42 nM active polymerase). The solutions with the $P_{N25}$ promoter fragment, and the RNAP were combined and the association reaction was started by mixing the batches.

After incubation at 37° C. for 10 seconds, 300 µl of BB solution containing 0.8 µg of single-stranded M13mp8-DNA, incubated at 37° C. for 2 minutes, were added. After incubation at 37° C. for 5 minutes, the batch, as described previously, was filtered at 37° C. over nitrocellulose, the filter was rinsed with 200 µl of BB containing 40 mM KCl and the filter-bound radioactivity was determined.

Figure 15:
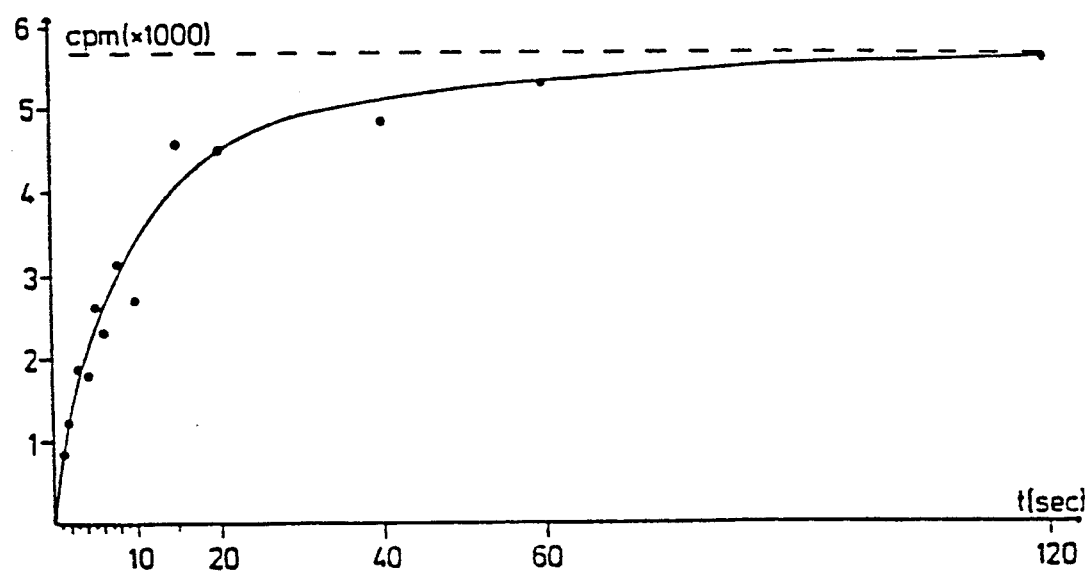

Eleven additional experiments were carried out under the same conditions in which the association reactions were stopped after 1, 2, 3, 4, 5, 6, 7, 8, 15, 20, 60 and 120 seconds, by the addition of single-stranded M13mp8-DNA. The numerical values obtained from all 12 experiments were plotted against reaction time as shown in FIG. 15, where the dotted line represents the maximal radioactivity which can be filter-bound. For the determination of this value, 50 µl of $P_{N25}$ promoter fragment were incubated at 37° C. for 3 minutes with 100 µl of BB containing 120 mM KCl and 1 pMole of active polymerase. Thereafter, the reaction was stopped and the batch was worked-up as above described above.

The maximal bindable radioactivity ($A_O$) corresponds to the amount of promoter fragments used (or 100% RNAP/$P_{N25}$ complexes). The difference between $A_O$ and the bound radioactivity (X) at time t is a relative measurement for the free promoter fragment at time t. The expression $(A_O-X)/A_O$ thus gives the amount of free promoter fragment at time t. The expression $-\ln[(A_O-X)/A_O]$ was calculated for all partial experiments and plotted against the reaction time t (see FIG. 16). The slope m of the regression line corresponds to the velocity constants m of equations (3) and (4) from paragraph 1 and was calculated to be m=0.12/second. For an active polymerase concentration of 0.42 nM (determined as in paragraph B, 4), a $K_a$ of $2.8 \times 10^8$ $M^{-1}$ sec$^{-1}$ was obtained using the relationship $K_a$=m/R (equation (2) in paragraph 1).

Experiments 2 and 3

Experiments 2 and 3 were carried out in a manner analogous to Experiment 1, in which the reactants based on the reaction solutions were present in the following concentrations:

| Experiment 2 | Promotor fragment $P_{N25}$: | 0.02 nM |
|---|---|---|
| | Active RNAP: | 0.32 nM |
| | Reaction times | 2, 4, 8, 10, 15, 20 and 60 seconds |
| Experiment 3 | Promotor fragment $P_{N25}$: | 0.02 nM |
| | Active RNAP: | 0.15 nM |
| | Reaction times | 2, 4, 8, 10, 15, 20 and 60 seconds |

Figure 17:
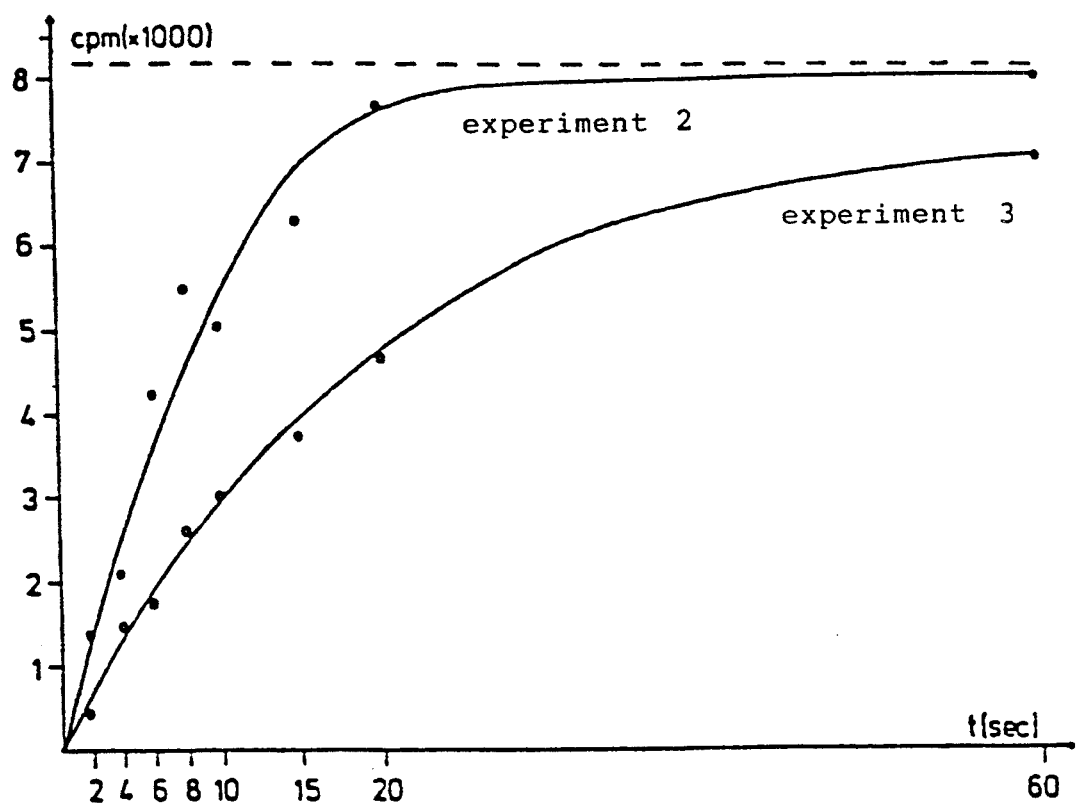

The numerical values were evaluated (see FIG. 17 and 18) as described for Experiment 1, whereby the following values were determined:

Experiment 2 m=0.104/sec.:

$$K_a = 3.2 \times 10^8 \, M^{-1} \, sec^{-1}$$

Experiment 3 m=0.04/sec.:

$$K_a = 2.7 \times 10^8 \, M^{-1} \, sec^{-1}$$

Averaging the results of the three experiments, the $K_a$ for RNAP and promoter $P_{N25}$ was found to be $2.9 \times 10^8$ $M^{-1}$ sec$^{-1}$.

This value is subject to an error of approximately 15% since there are errors of measurement in the concentration determination of promoter fragments and selective RNAP and in the filter binding experiments of about 10%.

C. Determination of the Association Rates for RANP and Various Expression Control Sequences By Relative Measurements With Promotors $P_{N25}$ and $P_{AI}$ as Internal Standards 1. Theory The complex formation rates for RNAP and the expression control sequences tacOP29, N25*/O, N25OP29, N25OPSN25Op29, AI, A1OPSAL, A1OP-SCONA1, AlpOPSAL and OPA1OPSA1 were determined by relative measurements using promoters $P_{N25}$ and $P_{AI}$ as internal standards. The following factors were considered in making these determinations.

Different promoters in a mixture compete according to their complex formation rates with RNAP, when RNAP is present in excess.

The change in promoter concentration per unit time of a bimolecular reaction of the second order between RNAP and promoter is defined by equation (1), $dP/dt = -K_a \times R \times P$, for formed complexes having a high half life.

In a reaction mixture containing different promoters, the concentration of free RNAP at any point in time is the same for all promoters. Accordingly, the following relationships apply for two promoters a and b having association rates $K_{a,a}$ and $K_{a,b}$:

$$-dP_a/P_a \times 1/K_{a,a} = R \times dt$$

$$-dP_b/P_b \times 1/K_{a,b} = R \times dt$$

Since $R \times dt$ is the same for both promoters, $$-dP_a/P_a \times 1/K_{a,a} = -dP_b/P_b \times 1/K_{a,b}$$

or, $$-dP_a/P_a = -K_{a,a}/K_{a,b} \times dP_b/P_b.$$

After integration:

$$-\ln[(A_O-x)/A_O] = -K_{a,a}/K_{a,b} \times \ln[(B_O-y)/B_O]$$

or $$K_{a,b} = K_{a,a} \times -\ln[(B_O-y)/B_O]/-\ln[(A_O-x)/A_O] \quad (6),$$

with $A_O$ and $B_O$ being the total amount of promoters a and b, respectively, bound in the RNAP excess, and with x and y being the amount of complexes from RNAP and promoter a and from RNAP and promoter b, respectively, formed in the RNAP excess.

2. Determination of Association Rates with Promoter $P_{N25}$ as the Internal Standard Radioactively-labelled DNA fragments having the corresponding expression control sequences (see Example 2) were incubated in parallel batches in a volume of 30 μl with different amounts of RNAP for 2 minutes at 37° C. in binding buffer. Then, 20 μl of binding buffer (37° C.) with 1 μg of single-stranded M13mp8-DNA were added to stop the association reaction. After a further 2 minutes at 37° C., the batches were filtered through a nitrocellulose filter.

The complexes retained on the filter were eluted and, after extraction with phenol, precipitated with ethanol. The DNA was taken up in 30 μl of sample buffer, and a third of the DNA was electrophoresed in 6% polyacrylamide gels with 8.3M urea and visualized via autoradiography as described by Maniatis et al., supra.

For each ratio of RNAP to promoter, the amount of bound promoter (X for $P_{N25}$, Y for the promoter to be measured) was determined for each promoter. For this purpose, the individual traces in the autoradiograms, which in each case corresponded to an experiment with a specific amount of RNAP, were measured densitometrically at a wavelength of 400 nm in an Elscript 400 densitometer (Hirschmann, Unterhachingen, BRD). From traces whose ratio of RNAP to promoter was greater than/equal to 1, average values for the total amounts of promoters capable of binding ($A_O$ for $P_{N25}$, $B_O$ for the promoter to be measured) were obtained.

To determine the association rates, the values for $-\ln((A_O-x)/A_O)$ and $-\ln((B_O-y)/B_O)$ were calculated and plotted against one another for each RNAP/-promoter ratio. The slope of the lines m obtained corresponds to the expression $-\ln((B_O-y)/B_O]/-\ln[(A_O-x)/A_O]$ from equation (6). With the aid of this value and the association rate of promoter $P_{N25}$, the association rate for the measured promoter was obtained using equation (6).

To determine the association rate for promoter Al, seven parallel batches were incubated with approximately 0.02 pMole of fragment having promoter $P_{N25}$ (~10,000 cpm) and approximately 0.02 pMole of fragment having promoter $P_{Al}$ (~10,000 cpm), with different amounts of RNAP (0.004–0.012 pMole). The RNAP/promoter ratios, the densitometric values obtained and the values calculated therefrom are presented in Table 1 for the individual experiments.

TABLE 1

| RNAP/Promoter Ratio | Densitometric Values[b] For $P_{N25}$ | Densitometric Values[b] For $P_{A1}$ | Values For $-\ln[(A_O-x)/A_O]$ | Values For $-\ln[(B_O-y)/B_O]$ |
|---|---|---|---|---|
| 3 | 25,338[a] | 26,844[a] | | |
| 1.5 | 30,331[a] | 30,510[a] | | |
| 1.0 | 25,361[a] | 22,977[a] | | |
| 0.5 | 23,085 ($x_1$) | 71,586 ($y_1$) | 1.97 | 1.05 |
| 0.3 | 15,729 ($x_2$) | 10,843 ($y_2$) | 0.89 | 0.51 |
| 0.2 | 13,226 ($x_3$) | 9,296 ($y_3$) | 0.67 | 0.41 |
| 0.1 | 7,203 ($x_4$) | 3,535 ($y_4$) | 0.31 | 0.14 |

Figure 19:
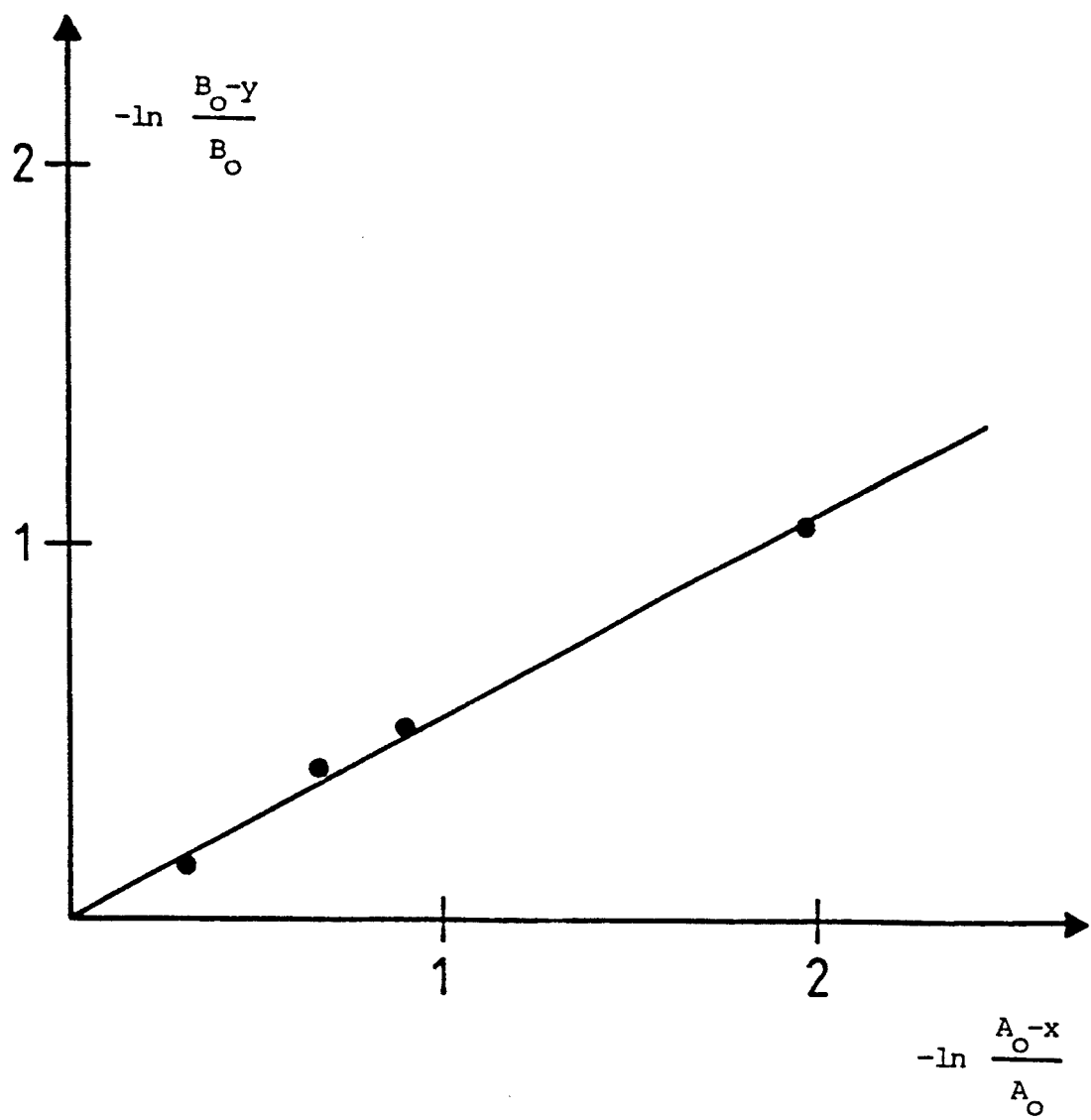

[a]Values for determining the average value $A_O$ and $B_O$, respectively, of promoter PN25 and PA1, respectively.
[b]400 nm reading of Elscript 400 densitometer The values presented in Table 1 are represented graphically in FIG. 19. The value m=0.5 was obtained for the slope of the lines. Using that value and equation (6):

$$K_{a,Al} = K_{a,N25} \times m \quad (K_{a,N25} = 2.9 \times 10^8 \, M^{-1} \, sec^{-1})$$

$$K_{a,Al} = 2.9 \times 0.5 \times 10^8 \, M^{-1} \, sec^{-1}$$

$$K_{a,Al} = 1.5 \times 10^8 \, M^{-1} \, sec^{-1}$$

The following association rates were obtained for the remaining expression control sequences.

tacOP29:

$$K_a = 0.85 \times 10^8 \, M^{-1} \, sec^{-1}$$

N25*/0:

$$K_a = 2.9 \times 10^8 \, M^{-1} \, sec^{-1}$$

N25OP29:

$$K_a = 2.9 \times 10^8 \, M^{-1} \, sec^{-1}$$

N25OPSN25OP29:

$$K_a = 2.9 \times 10^8 \, M^{-1} \, sec^{-1}$$

These values are subject to an error of approximately 15%.

3. Determination of the Association Rates with Promotor $P_{Al}$ as the Internal Standard The association rates of the expression control sequences A1OPSA1, A1OPSCONA1, AlpOPSA 1 and OPA1OPSA1 were determined with promoter $P_{Al}$ as the internal standard as described in paragraph C.2. To determine the association rate for element A1OPSA1, the RNAP/promoter ratios, the densitometric values obtained and the values calculated therefrom were obtained from four parallel experiments carried out with different amounts of RNAP, with the results shown in Table 2:

TABLE 2

| RNAP/Promoter Ratio | Densitrometric Values[a] For $P_{N25}$ | Densitrometric Values[a] For $P_{A1}$ | Values For $-\ln[(A_O-x)/A_O]$ | Values For $-\ln[(B_O-y)/B_O]$ |
|---|---|---|---|---|
| 3 | 61,856 ($A_O$) | 69,018 ($B_O$) | 0.00 | 0.00 |
| 0.5 | 41,477 | 24,983 | 1.11 | 0.45 |

TABLE 2-continued

| RNAP/ Promoter Ratio | Densitometric Values[a] For | | Values For | |
|---|---|---|---|---|
| | $P_{N25}$ | $P_{A1}$ | $-\ln[(A_O\text{-}x)/A_O]$ | $-\ln[(B_O\text{-}y)/B_O]$ |
| 0.2 | (x₁) 22,484 | (y₁) 9,054 | 0.45 | 0.14 |
| 0.1 | (x₂) 11,303 | (y₂) 5,517 | 0.20 | 0.08 |
| | (x₃) | (y₃) | | |

[a]400 nm reading of Elscript 400 densitometer

Figure 20:
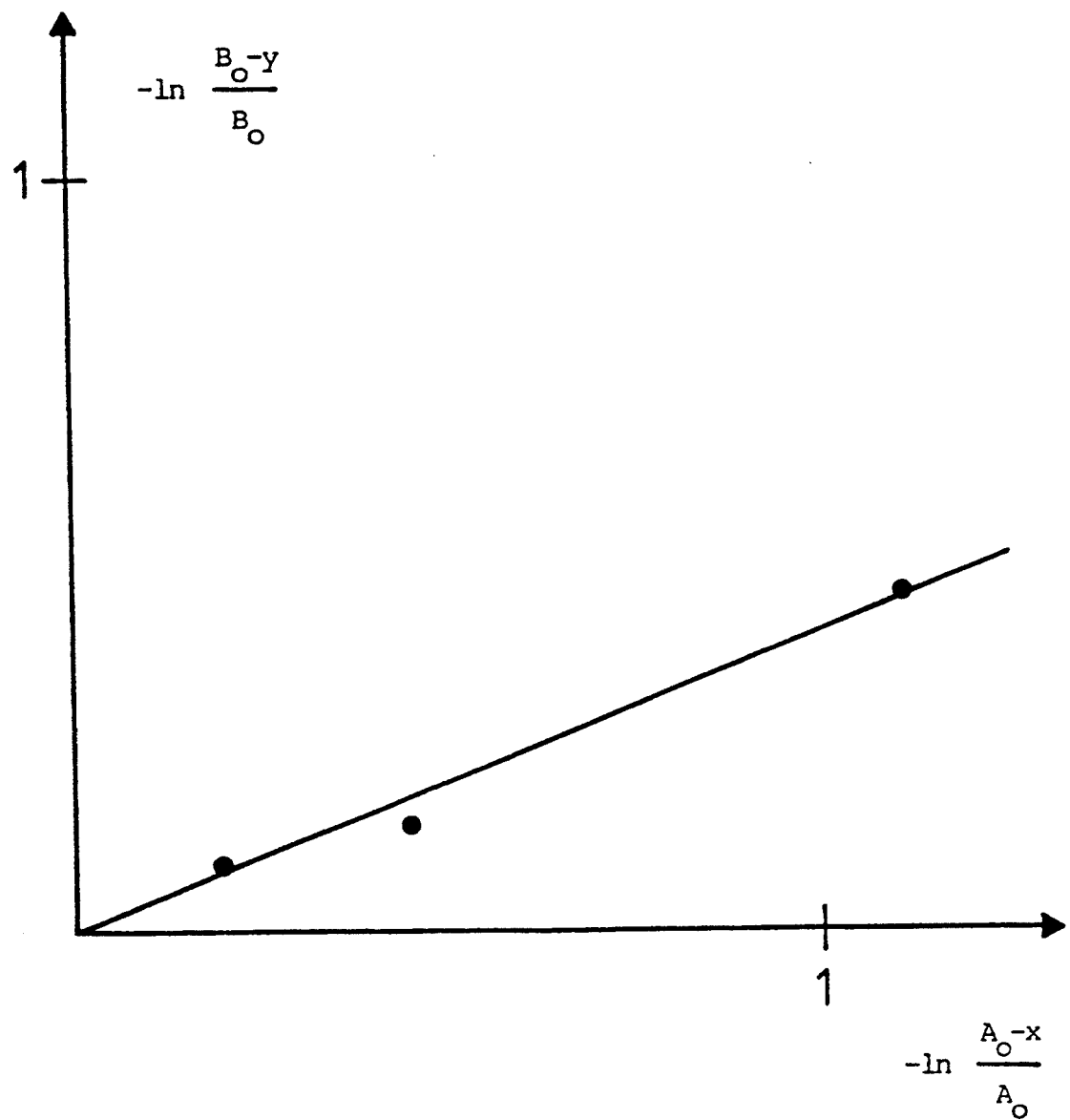

The values presented in Table 2 are represented graphically in FIG. 20. The value m=0.4 was obtained for the slope of the lines. Using that value and equation (6):

$$K_{a, A1}\text{OPSA1} = K_{a,A1} \times m(K_{a, A1} = 1.5 \times 10^8 \ M^{-1} sec^{-1})$$

$$K_{a, A1}\text{OPSA1} = 1.5 \times 0.4 \times 10^8 \ M^{-1} sec^{-1}$$

$$K_{a, A1}\text{OPSA1} = 0.6 \times 10^8 \ M^{-1} sec^{-1}$$

The following association rates were obtained for the remaining expression control sequences:

A1OPSCONA1:

$$K_a = 1.7 \times 10^8 \ M^{-1} sec^{-1}$$

A1pOPSA1:

$$K_a = 0.6 \times 10^8 \ M^{-1} sec^{-1}$$

OPA1OPSA1:

$$K_a = 0.6 \times 10^8 \ M^{-1} sec^{-1}$$

These values are subject to an error of approximately 15%.

Example 4

Determination of the In Vivo Promoter Strengths (induced) of the Expression Control Sequences A. Principles The in vivo promoter strengths of the expression control sequences were determined relative to the promoter for the β-lactamase gene ($P_{bla}$), using that promoter as an internal standard according to the procedure of Deuschle et al., supra. For this purpose, pDS3 derivatives containing the corresponding expression control sequences were transformed into E. coli M15 cells which contained plasmid pDMI,1. Radioactively labelled RNA, synthesized in the presence of IPTG (inductor) during a specified time, was then isolated from cultures of these transformants and hybridized in separate batches against the following single-stranded DNA, probes present in excess: 1) M13mp9dhfr-DNA, 2) M13mp9bla-DNA and 3) M13mp9-DNA, as the control. After RNase treatment to degrade non-hybridized RNA the batches were filtered through a nitrocellulose filter.

Since RNA/DNA hybrids are retained on nitrocellulose, the filter-bound radioactivity was a measurement of the amount of RNA present in the individual batches, which was complimentary to the DNA probes used. After deducting the radioactivity bound in the control (single-stranded M13mp9-DNA), the ratio of radioactivity bound by single-stranded M13mp9dhfr-DNA (the corresponding RNA was synthesized under control of the expression control sequence to be measured) to radioactivity bound by single-stranded M13mp9bla-DNA (this RNA was synthesized under control of $P_{bla}$) was determined. After a necessary correction this ratio gave the promoter strength of the measured expression control sequence in $P_{bla}$ units.

B. Production of Single-stranded M13mp9, M13mp9dhfr and M13mp9bla Phage DNAs

To produce phage M13mp9dhfr, the BamHI-HindIII fragment of plasmid pDS1,t₀1+, containing the dhfr gene, was integrated into the DNA of phage M13mp9 (Pharmacia Sweden; cleaved with BamHI and HindIII) according to known methods (Maniatis et al., supra). Phage M13mp9bla was produced in an analogous manner, whereby the EcoRI-PstI fragment from plasmid pDS1,t₀1+ was integrated with parts of the bla gene in DNA of phage M13mp9 (cleaved with EcoRI and PstI). Thereafter, single-stranded M13mp9-DNA, M13mp9dhfr-DNA and M13mp9bla-DNA was produced in a manner analogous to that described in Example 3 for the production of single-stranded M13mp8-DNA.

C. Determination of In Vivo Promotor Strengths (induced)

The determination of the promoter strengths was carried out as follows according to the procedure of Deuschle et al., supra:

1) Production of In Vivo Labelled ³H-RNA

E. coli M15 cells containing plasmid pDMI,1, and a pDS3 derivative containing one of the various expression control sequences (see Example 2), were stored at −20° C. in 20% glycerol. 10 ml of LB medium containing 100 μg/ml ampicillin and 25 μg/ml kanamycin were inoculated with one of these stock cultures and grown at 37° C. overnight in a shaking incubator (180 rpm). 0.1 ml of this overnight culture was diluted in 25 ml of M9 minimal medium (Miller, supra), containing 5% casein hydrolysate, 0.1% bactotryptone, 0.05% yeast extract, 0.05% NaCl, 0.5% glycerol, 1 mM IPTG, 100 μg/ml ampicillin and 25 μg/ml kanamycin, which had been pre-warmed to 37° C. The cells were grown at 37° C. in a shaking incubator (250 rpm) to an optical density of $OD_{600} = 0.6$.

To 10 ml of this culture were added 0.5 mCi of 5,6-³H-uridine (40–60 mCi/mmol, 1 mCi/ml aqueous solution; Amersham, Braunschweig, FRG). After 45 seconds the culture was cooled rapidly to 0° C. with liquid nitrogen and the cells were centrifuged and re-suspended in TES buffer (20 mM Tris-HCl, pH 8.0, 10 mM EDTA, 100 mM NaCl, 1% SDS). After incubation at 95° C. for 3 minutes, the resulting mixture of lysed cells was centrifuged as described by Glisin et al. (Biochemistry 13, 2633–2637 [1974]) (CsCl gradient centrifugation, 150,000× g, 16 hours, 20° C.).

After removing the supernatant the centrifuge test tubes were cut 0.8 cm above the bottom with a heated scalpel. The RNA in the bottom part of the test tube was dissolved with 2×80 μl of TE buffer containing 0.2% SDS and precipitated with ethanol in the presence of 3M sodium acetate. The precipitate was washed with 80% ethanol, dried in a vacuum and dissolved in hybridization buffer (see below). As a rule, 200–300 μg of RNA having a specific activity of 1–3×10⁵ cpm/μg RNA were obtained from 10 ml of culture.

2. Hybridization of the RNA to An Excess of Single-stranded DNA

All hybridizations were carried out for 2 hours at 42° C. in 20 μl of hybridization buffer (50% formamide, 300 mM NaCl, 20 mM Tris-HCl, pH 8.0, 0.5 mM EDTA).

In a typical experiment, 10 μl of the in vivo ³H-RNA (~5×10⁵ cpm) were mixed with 10 μl of single-stranded M13mp9-DNA (0.2 pMoles, control), M13mp9dhfr-DNA (0.2 pMoles) and M13mp9bla-DNA (0.2 pMoles), respectively, incubated at 65° C. for 3 minutes and then held at 42° C. for 2 hours.

3) Quantification of the Hybridized RNA

The hybridization batches were diluted ten-fold with 2×SSC buffer and filtered through a nitrocellulose filter (0.45 μm BA85 filter, minifold system, Scheicher and Schüll, FRG). The capacity of the filter used for single-stranded M13mp9-DNA was approximately 6 pMole/cm². The filter was washed with 2 ml of 2×SSC buffer, baked at 80° C. for 30 minutes in a vacuum and then incubated for 1 hour at 42° C. in 100 ml of 2×SSC buffer containing 50 μg/ml of RNase A. Subsequently, the filter was washed three times with 100 ml of 2×SSC buffer during 10 minutes at 42° C. After drying the filter, the radioactivity retained was counted in a scintillation liquid ("universal liquid scintillator", NEN). The ratio of dhfr- to bla-specific RNA was calculated taking into account the number of uridines within the various RNAs. Since the single-stranded DNA inserts specific for dhfr and bla code respectively for 169 and 148 uridines (148/169=0.87), the in vivo promoter strength S of a desired expression control sequence in $P_{bla}$ units is obtained using the formula:

$$S = 0.87 \times (cpm_{dhfr} - cpm_{control})/(cpm_{bla} - cpm_{control}).$$

D. In Vivo Promoter Strengths of the Expression Control Sequences

Determination of the in vivo promoter strength for each of the various expression control sequences was carried out at least three times as described in paragraph C, whereby the radioactively labelled RNA synthesized was determined in each case twice. For the expression control sequence A1OPSA1, the following values in the determination of the synthesized RNA were obtained:

| Measurement No. | M13mp9-DNA | Single stranded M13mp9dhrf-DNA | M13mP9bla-DNA |
|---|---|---|---|
| 1 | 38 | 33,581 | 839 |
| 2 | 22 | 36.099 | 831 |

Using the foregoing data, the following values were obtained for the in vivo promoter strengths:

$S_1 = 0.87 \times (33{,}581 - 38)/(839 - 38) = 36.4$ $P_{bla}$ units.

$S_2 = 0.87 \times (36{,}099 - 22)/(831 - 22) = 38.8$ $P_{bla}$ units.

An in vivo promoter strength of 37.6 $P_{bla}$ units was calculated as the average value.

Averaged over a total of three determinations, a promoter strength of 38.1±3.4 $P_{bla}$ units was calculated for the expression control sequence A1OPSA1. The promoter strengths determined as described previously for all tested expression control sequences are presented in Table 3.

TABLE 3

| Expression Control Sequence | In Vivo Promoter Strength Induced [Pbla units] |
|---|---|
| lacOP29 | 5.5 ± 1.0 |
| tacOP29 | 17.6 ± 1.8 |
| N25 | 26.2 ± 2.0 |

TABLE 3-continued

| Expression Control Sequence | In Vivo Promoter Strength Induced [Pbla units] |
|---|---|
| N25*/O | 8.0 ± 1.5 |
| N25OP29 | 7.7 ± 1.3 |
| N25OPSN25OP29 | 9.3 ± 1.2 |
| A1 | 66.1 ± 2.5 |
| A1OPSA1 | 38.1 ± 3.4 |
| A1OPSCONA1 | 16.8 ± 2.0 |
| A1POPSA1 | 25.1 ± 1.3 |
| OPA1OPSA1 | 38.1 ± 3.4 |
| A1OPSA10P21 | 32.9 ± 5.0 |
| A1OPSA10P29 | 31.5 ± 3.0 |

Example 5

Determination of the Repression Factor of the Various Expression Control Sequences A. Principles The repression factors, i.e., the ratio of the in vivo promoter strengths under induced and repressed conditions for the individual expression control sequences, were determined as follows:

a) Expression Control Sequences Having a Repression Factor of Less Than 100

The expression control sequences tacOP29, N25*/O, N25OP29, OPUA1 and OPUA1CON initiated transcription of sufficient amounts of RNA in vivo under repressed conditions (excess of repressor, no inducer) so that they could be determined directly. The repression factors were then calculated using the values determined in Example 4 for the in vivo promoter strengths (induced).

b) Expression Control Sequences Having a Repression Factor of Greater Than 100

The in vivo promoter strengths for the expression control sequences lacOP29, N25OPSA25OP29, A1OPSA1, A1OPSA1OP21, A1OPSA1OP29, A1OPSCONA1, A1pOPSA1 and OPA1OPSA1 were determined indirectly under repressed conditions. For this purpose, for the individual elements the amount of β-galactosidase which was produced in a suitable system under repressed conditions was first determined by means of an enzymatic test. The values obtained were then converted into $P_{bla}$ units by means of a correction factor. The repression factors were then calculated using the values determined in Example 4.

Direct Determination of the In Vivo Promoter Strengths ($P_{bla}$ units) of the Expression Control Sequences Under Repressed Conditions The in vivo promoter strengths under repressed conditions were determined as described in Example 4, but without the addition of IPTG. The values obtained are compiled in Table 4:

TABLE 4

| Expression Control Sequence | Promotor Strengths Repressed [$P_{bla}$ units] |
|---|---|
| tacOP29 | 0.36 ± 0.02 |
| N25OP29 | 1.5 ± 0.1 |
| N25*/O | 1.5 ± 0.1 |
| OPUAI | 2.7 ± 0.5 |
| OPUA1CON | 1.7 ± 0.6 |

C. Indirect Determination of the In Vivo Promoter Strengths of the Expression Control Sequences Under Repressed Conditions 1. Determination of β-Galactosidase Units The pML3 derivatives having the expression control sequences lacOP29, tacOP29, N25OP29, N25OPSN-25OP29, A1OPSA1, A1OPSA1OP21, A1OPSA1OP29, A1OPSCONA1, AlpOPSA1, OPA1OPSA1, OPUA1 and OPUA1CON were transformed into E. coli M15 cells as described by Maniatis et al., supra. The transformed E. coli M15 cells obtained having the corresponding plasmids were then grown to the logarithmic phase, and the amount of β-galactosidase was determined according to the procedure of Miller ("Experiments in Molecular Genetics", Cold Spring Harbor, N.Y., 1972). One such determination is described below as an example for the expression control sequence N25OP29.

10 ml of supplemented minimal medium (Miller, supra) were inoculated with 0.05 ml of an overnight culture of transformed E. coli M15 cells containing plasmid pML3/N25OP29 and incubated at 37° C. in a shaking incubator (200 rpm). After attaining an $OD_{600}$ (optical density at a wavelength of 600 nm) of 0.55, the culture was placed on ice for 20 minutes, after which the optical density was again determined. A value of $OD_{600}=0.607$ was obtained. 0.1 ml of the culture were then diluted with Z buffer (Miller, supra) to a final volume of 1 ml. This sample was treated as follows, together with a control (1 ml of Z buffer):

Addition of 60 μl of chloroform and 30 μl of 0.1% SDS (cell rupture);

mixing of the sample for 10 seconds by means of a vortex;

incubation of the sample at 28° C. for 5 minutes;

addition of 200 μl of ONPG (Miller, supra);

mixing of the sample by means of a vortex;

incubation of the sample at 28° C. until a yellow color was visible;

addition of 250 μl of 2M $Na_2CO_3$ (the time between the addition of ONPG and $Na_2CO_3$ amounted to 1.5 minutes);

mixing the sample by means of a vortex;

centrifugation of the cell fragments (Eppendorf bench centrifuge, 13000 rmp 5 minutes); and determination of the extinction at 420 nm against the control.

A value of $\Delta E_{420}=0.737$ was obtained. According to the formula described by Miller, supra:

$$\beta\text{-Galactosidase units} = 1000 \times \Delta E_{420}/OD_{600} \times V \times t$$

wherein $\Delta E_{420}$ is the $E_{420}$ measured value of the reaction batch against the control (0.737), $OD_{600}$ is the cell density of the culture sample used (0.607), t is the reaction time (1.5 minutes) and V is the volume of culture used (0.1 ml), 8,094 β-galactosidase units were calculated. Averaged over 8 experiments 8,160±450 β-galactosidase units were obtained.

The values obtained for all measured expression control sequences are compiled in Table 5, whereby at least 4 measurements were carried out for each expression control sequence.

TABLE 5

| Expression Control Sequence | β-Galactosidase Units |
|---|---|
| lacOP29 | 30 ± 5 |
| tacOP29 | 1510 ± 170 |
| N25OP29 | 8160 ± 450 |

TABLE 5-continued

| Expression Control Sequence | β-Galactosidase Units |
|---|---|
| N25OPSN25OP29 | 99 ± 6 |
| A1OPSA1 | 110 ± 2 |
| A1OPSCONA1 | 220 ± 12 |
| A1POPSA1 | 58 ± 3 |
| OPA1OPSA1 | 56 ± 1 |
| OPUA1 | 13700 ± 3000 |
| OPUA1CON | 8500 ± 2000 |
| A1OPSA1OP29 | 23 ± 3 |
| A1OPSA1OP21 | 15 ± 3 |

Figure 21:
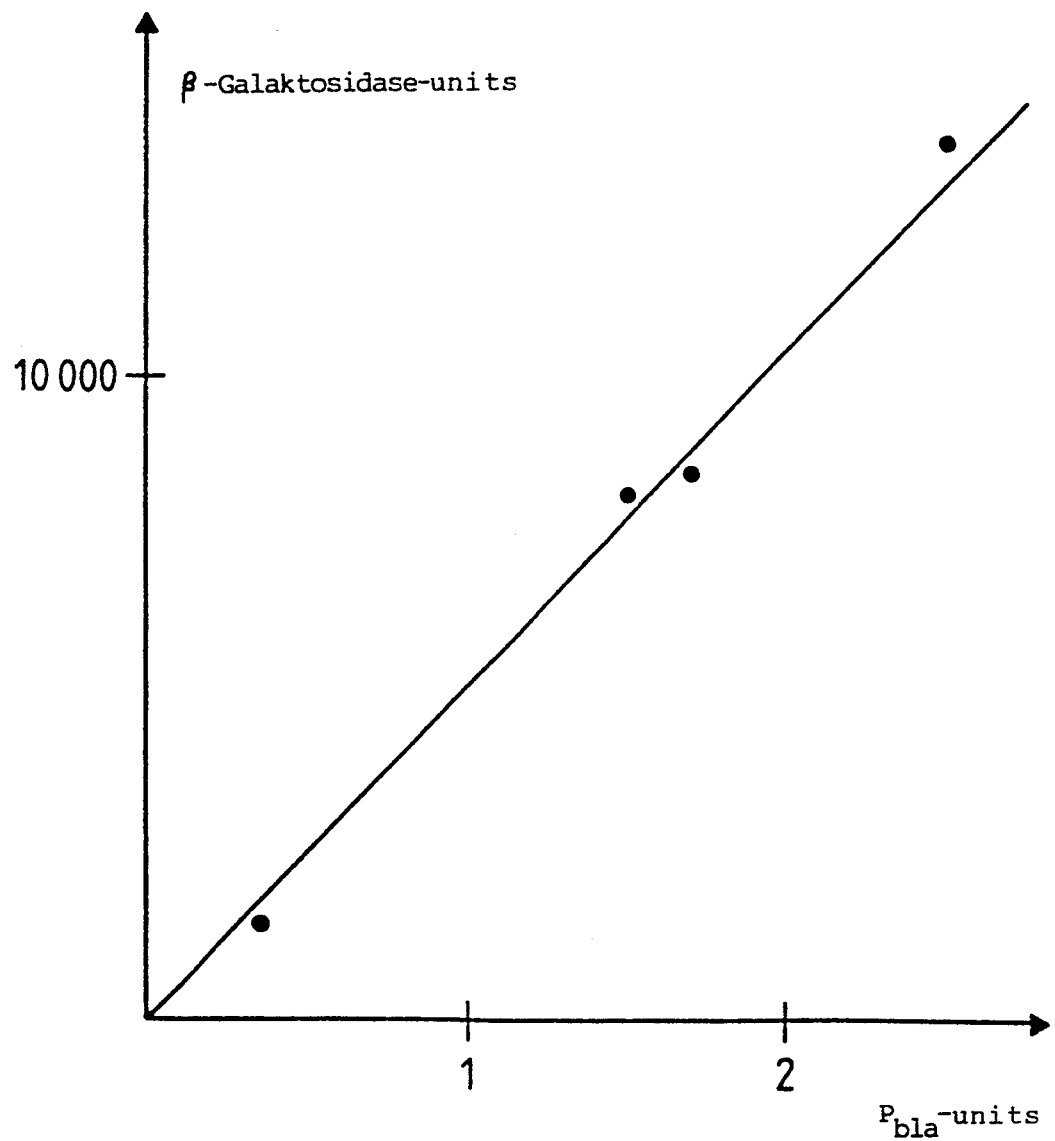

2. Determination of the Factor For the Conversion of β-Galactosidase Units Into $P_{bla}$ Units The in vitro promoter strengths under repressed conditions for the expression control sequences tacOP29, N25OP29, OPUA1 and OPUA1CON could be determined directly ($P_{bla}$ units, Table 4) and indirectly (β-galactosidase units, Table 5). The values obtained are plotted against each other in FIG. 21. The slope of the regression line is a measurement for the conversion of β-galactosidase units into $P_{bla}$ units. A value of 5,000 β-galactosidase units/$P_{bla}$ unit was obtained.

3. Conversion of β-Galactosidase Units in $P_{bla}$ Units

The $P_{bla}$ units (Table 6) were calculated for the corresponding expression control sequences from the measured β-galactosidase units (Table 5) using the conversion factor 5,000 β-galactosidase units/$P_{bla}$ unit.

TABLE 6

| Expression Control Sequence | β-Galactosidase Units | $P_{bla}$ Units |
|---|---|---|
| lacOP29 | 30 ± 5 | 0.006 ± 0.001 |
| N25OPSN25OP29 | 99 ± 6 | 0.02 ± 0.003 |
| A1OPSA1 | 110 ± 2 | 0.022 ± 0.001 |
| A1OPSCONA1 | 220 ± 12 | 0.044 ± 0.003 |
| AIPOPSAI | 58 ± 3 | 0.012 ± 0.001 |
| OPA1OPSA1 | 56 ± 1 | 0.011 ± 0.001 |
| A1OPSA10P29 | 23 ± 3 | 0.0046 ± 0.0006 |
| A1OPSA10P21 | 15 ± 3 | 0.003 ± 0.0006 |

D. Calculation of the Repression Factors

The values listed in Tables 3, 4 and 6 were used to calculate the repression factors ($P_{bla}$ units, induced/$P_{bla}$ units, repressed) for the individual expression control sequences (Table 7).

TABLE 7

| | In Vivo Promoter Strengths | | |
|---|---|---|---|
| Expression Control Sequence | $P_{bla}$ Units Induced | $P_{bla}$ Units Repressed | Repression Factor |
| lacOP29 | 5.5 ± 1.0 | 0.006 ± 0.001 | 920 ± 230 |
| tacOP29 | 17.6 ± 1.8 | 0.36 ± 0.02[a] | 49 ± 6 |
| N25*/O | 8.0 ± 1.5 | 1.5 ± 0.1[a] | 5.3 ± 2 |
| N25OP29 | 7.7 ± 1.3 | 1.5 ± 0.1[a] | 5.1 ± 2 |
| N25OPSN25OP29 | 9.3 ± 1.2 | 0.02 ± 0.003 | 465 ± 92 |
| A1OpSA1 | 38.1 ± 3.4 | 0.022 ± 0.001 | 1730 ± 170 |
| A1OPSCONA1 | 16.8 ± 2.0 | 0.044 ± 0.003 | 380 ± 50 |
| A1POPSA1 | 2.51 ± 1.3 | 0.012 ± 0.001 | 2090 ± 240 |
| OPA1OPSA1 | 38.1 ± 3.4 | 0.011 ± 0.001 | 3460 ± 460 |
| A1OPSA10P29 | 3.15 ± 3.0 | 0.0046 ± 0.0006 | 6850 ± 610 |
| A1OPSA10P21 | 32.9 ± 5.0 | 0.003 ± 0.0006 | 10970 ± 2000 |

[a] direct determination of the in vivo promoter strength

E. Compilation of the Characteristic Properties of the Individual Expression Control Sequences The values for the in vitro association rate, the in vivo promoter strength and the repression factor obtained for the individual expression control sequences are shown in Table 8.

TABLE 8

| Expression Control Sequence | In Vitro Complex Formation Rate ($K_a$) [$10^8 M^{-1} sec^{-1}$] (Signal strength) | In Vivo Promoter Strengths Repressed [$P_{bla}$-units] | Induced [$P_{bla}$ units] | Repression Factor |
|---|---|---|---|---|
| lacOP29 | 0.02[a] | 0.006 ± 0.001 | 5.5 ± 1.0 | 920 ± 230 |
| tacOP29 | 0.85 | 0.36 ± 0.02 | 17.6 ± 1.8 | 49 ± 6 |
| N25 | 2.9 | — | 26.2 ± 2.0 | — |
| N25*/0 | 2.9 | 1.5 ± 0.1 | 8.0 ± 1.5 | 5.3 ± 2 |
| N25OP29 | 2.9 | 1.5 ± 0.1 | 7.7 ± 1.3 | 5.1 ± 2 |
| N25OPSN25OP29 | 2.9 | 0.2 ± 0.003 | 9.3 ± 1.2 | 465 ± 92 |
| A1 | 1.5 | — | 66.1 ± 2.5 | — |
| A1OPSA1 | 0.6 | 0.022 ± 0.001 | 38.1 ± 3.4 | 1730 ± 170 |
| A1OPSC0NA1 | 1.7 | 0.044 ± 0.003 | 16.8 ± 2.0 | 380 ± 50 |
| A1pOPSA1 | 0.6 | 0.012 ± 0.001 | 25.1 ± 1.3 | 2090 ± 240 |
| APA10PSA1 | 0.6 | 0.011 ± 0.001 | 38.1 ± 3.4 | 3460 ± 460 |
| A1OPSA1OP29 | N.D. | 0.0046 ± 0.0006 | 31.5 ± 3.0 | 6850 ± 610 |
| A1OPSA1OP21 | N.D. | 0.003 ± 0.006 | 32.9 ± 5.0 | 10970 ± 2000 |

[a]Literature value from McClure et al. ("Promoters, Structure and Function", Hrsg. Rodriguez and Chamberlin, Praeger, pages 111-120 [1982])
N.D. = Not determined

What is claimed is:

1. A DNA expression control sequence comprising a T-coliphage promoter sequence having a low signal strength in the induced state and a high in vivo promoter strength combined with a lac-operator sequence from a lac-operator/repressor system wherein said system has a high association rate prior to said combination with said promoter.

2. The expression control sequence of claim 1 which contains a T7A1 promoter and a lac-operator sequence.

3. The expression control sequence of claim 2 which is A1OPSA1 and contains the nucleotide sequence

```
CTCGAGAAAA TTTATCAAAA AGAGTGTTGA CTTGTGAGCG GATAACAATG
ATACTTAGAT TCATCGAGAG GGACACGGCG AATTC.
```

4. The expression control sequence of claim 2 which is A1POPSA1 and contains the nucleotide sequence

```
CTCGAGAAAA TTTATCAAAA AGAGTGTTGA CTTGTGAGCG CTCACAATTG
ATACTTAGAT TCATCGAGAG GGACACGGCG AATTC.
```

5. The expression control sequence of claim 2 which is OPA1OPSA1 and contains the nucleotide sequence

```
GTCGACGTTG ATCCCCTAGA AATTGTGAGC GCTCACAATT TCTAGGGATT
TAACGGTACC GAGCTTGTGG CAGTTTAAGG CGGGCGTCCT GCCCGCCACC
CTCCGGGCCG TTGCTTCGCA ACGTTCAAAT CCGCTCCCGG CGGATTTGTC
CTACTCAGGA GAGCGTTCAC CGACAAACAA CAGATAAAAC GAAAGGCCCA
GTCTTTCGAC TGAGCCTTTC GTTTTATTTG ATGCCTCAAG CTCGGTACCT
CGAGAAAATT TATCAAAAAG AGTGTTGACT TGTGAGCGGA TAACAATGAT
ACTTAGATTC ATCGAGAGGG ACACGGCGAA TTC.
```

6. The expression control sequence of claim 2 which is A1OPSA1OP21 and contains the nucleotide sequence

```
CTCGAGAAAA TTTATCAAAA AGAGTGTTGA CTTGTGAGCG GATAACAATG
ATACTTAGAT TCAATTGTGA GCGGATAACA ATTTCACACA GAATTC.
```

7. The expression control sequence of claim 2 which is A1OPSA1OP29 and contains the nucleotide sequence

```
CTCGAGAAAA TTTATCAAAA AGAGTGTTGA CTTGTGAGCG GATAACAATG
ATACTTAGAT TCAAATTGTG AGCGGATAAC AATTTGAATT C.
```

8. A DNA expression vector which can replicate in E. coli containing 1) an expression control sequence comprising a T-coliphage promoter sequence having a low signal strength in the induced state and a high in vivo promoter strength combined with a lac-operator sequence from a lac-operator/repressor system wherein said system has a high association rate prior to said combination with said promoter; and 2) a sequence which codes for the lac-repressor polypeptide of the lac-operator/repressor system.

9. A non-naturally occurring E. coli bacterium which contains a 1) an expression control sequence comprising a T-coliphage promoter sequence having a low signal strength in the induced state and a high in vivo promoter strength combined with a lac-operator sequence from a lac-operator/repressor system wherein said system has a high association rate prior to said combination with said promoter; and 2) a sequence which codes for the lac-repressor polypeptide of the lac-operator/repressor system.

10. A non-naturally occurring E. Coli bacterium, the chromosome of which has be modified to contain 1) a heterologous DNA expression control sequence comprising a T-coliphage promoter sequence having a low signal strength in the induced state and a high in vivo promoter strength combined with a lac-operator sequence from a lac-operator/repressor system wherein said system has a high association rate prior to combination with said promoter; and 2) a sequence which codes for the lac-repressor polypeptide of the lac-operator/-repressor system.

* * * * *